(12) United States Patent
Hayashi

(10) Patent No.: US 12,323,754 B2
(45) Date of Patent: Jun. 3, 2025

(54) HEADPHONE COVER AND FASTENER THEREFOR, AND HEADPHONE COVER MOUNTING METHOD

(71) Applicant: Fifty Square Inc., Tokyo (JP)

(72) Inventor: Masayuki Hayashi, Tokyo (JP)

(73) Assignee: Fifty Square Inc., Tokyo (JP)

( * ) Notice: Subject to any disclaimer, the term of this patent is extended or adjusted under 35 U.S.C. 154(b) by 330 days.

(21) Appl. No.: 18/041,874

(22) PCT Filed: Aug. 19, 2020

(86) PCT No.: PCT/JP2020/031248
§ 371 (c)(1),
(2) Date: Feb. 16, 2023

(87) PCT Pub. No.: WO2022/038706
PCT Pub. Date: Feb. 24, 2022

(65) Prior Publication Data
US 2023/0319451 A1     Oct. 5, 2023

(51) Int. Cl.
*H04R 25/00*     (2006.01)
*H04R 1/10*      (2006.01)

(52) U.S. Cl.
CPC .................. *H04R 1/1008* (2013.01)

(58) Field of Classification Search
CPC ....... H04R 1/1008; H04R 1/1058; H04R 1/12
(Continued)

(56) References Cited

U.S. PATENT DOCUMENTS

| 5,545,859 A | 8/1996 | Ullrich | |
| 11,683,622 B2* | 6/2023 | Hayashi | A61F 11/14 381/370 |

(Continued)

FOREIGN PATENT DOCUMENTS

| CN | 209017258 U | 6/2019 |
| JP | H0644290 A | 2/1994 |

(Continued)

OTHER PUBLICATIONS

Chinese Office Action issued on Mar. 30, 2024 for corresponding Chinese Application No. 202080103246.5.

(Continued)

*Primary Examiner* — Phylesha Dabney
(74) *Attorney, Agent, or Firm* — POLSINELLI PC

(57) ABSTRACT

Provided is a headphone cover configured such that an ear pad is covered with a fabric from the outer peripheral surface to the inner peripheral surface thereof, and a part of the fabric is fixed to the inner peripheral surface or the like of the ear pad using a fixing member 20 such that the recessed space formed in the middle portion of the ear pad is not closed. The fixing member 20 is formed of a belt-like member 21 having flexibility, a plurality of first locking portions 22 is formed on the upper surface of the belt-like member 21 while a second locking portion 23 is formed on the lower surface of the belt-like member. The fixing member is provided with a holding portion 24 for slidably holding a portion other than the rear end of the belt-like member 21. Then, the first locking portion 22 and the second locking portion 23 are formed in a shape in which the belt-like member 21 is slidable only in one direction in which the length from the rear end of the belt-like member 21 in the longitudinal direction to a portion held by the holding portion 24 is shortened in a state in which the portion of the belt-like member 21 is held by the holding portion 24 so that the headphone cover can be used on as many sizes of headphones as possible.

20 Claims, 13 Drawing Sheets

(58) Field of Classification Search
USPC .......................................................... 381/386
See application file for complete search history.

(56) References Cited

U.S. PATENT DOCUMENTS

| | | |
|---|---|---|
| 2008/0187151 A1 | 8/2008 | McClenon |
| 2019/0364356 A1 | 11/2019 | Lewis |
| 2022/0167070 A1* | 5/2022 | Hayashi .................. A61F 11/14 |

FOREIGN PATENT DOCUMENTS

| | | | |
|---|---|---|---|
| JP | 2015133609 A | 7/2015 | |
| TW | M594925 U | 5/2020 | |
| WO | WO-2020202535 A1 * | 10/2020 | ............. H04R 1/023 |

OTHER PUBLICATIONS

International Search Report and Written Opinion issued Oct. 27, 2020 for corresponding PCT Application No. PCT/JP2020/031248.

* cited by examiner

HEADPHONE COVER AND FASTENER THEREFOR, AND HEADPHONE COVER MOUNTING METHOD

CROSS REFERENCE TO RELATED APPLICATIONS

This application is a National Phase filing under 35 U.S.C. § 371 of PCT/JP2020/031248, filed on Aug. 19, 2020; the entire contents of which application is hereby incorporated by reference.

TECHNICAL FIELD

The present invention relates to a headphone cover and its fastener, and headphone cover mounting method, and more particularly, to a headphone cover used covering an ear pad (earmuff) of an around ear type headphone and a fastener for fastening the headphone cover to the ear pad.

BACKGROUND ART

Conventionally, a headphone cover used covering an ear pad of a headphone is known (see, for example, Patent Literature 1.). The headphone cover disclosed in Patent Literature 1 is a headphone cover formed by folding back a peripheral edge portion of a stretchable fabric to one surface side over the entire circumference of the peripheral edge portion and forming an opening in the one surface side and configured such that an elastic webbing is sewn to the fabric of an opening peripheral edge portion corresponding to the peripheral edge of the opening.

Attaching the headphone cover configured as described above to an ear pad makes it possible to eliminate discomfort caused by stickiness and stuffiness of the sweat and fat of the user using the headphone. That is, attaching the headphone cover made of a hygroscopic cloth to an ear pad makes it possible to reduce the stuffiness of the ear and prevent the discomfort caused by the stuffiness from occurring even when the user listens to music with the headphone for a long time.

Note that when a headphone cover is attached to an ear pad of an around ear type headphone (a type having a recessed space in the middle portion of an ear pad in which the ear is inserted and fitted (also called the over ear type)), the recessed space formed by the ear pad is blocked by the headphone cover, so that the sense of use is similar to that of an on-ear type headphone to which the ear is fixed by being pressed.

Patent Literature 1: JP 2015 -133609 A

SUMMARY OF INVENTION

Technical Problem

On the other hand, since the around ear type covers the entire ear, surrounding noise can be shut out to some extent and the ear comes close to the side of the loudspeaker, there is an advantage of allowing the user to hear a more powerful sound. Accordingly, there is a need for a user who uses the around ear type headphones to enjoy music with a sense of use similar to that of the around ear type even when the user attaches the headphone cover to the ear pad.

On the other hand, there is known a headphone cover used for an around ear type headphone, the headphone cover being configured to maintain a sense of use close to an around ear type even when the headphone cover is attached to an ear pad (see, for example, Patent Literature 2).

The headphone cover described in Patent Literature 2 includes a cover finished into a cylindrical shape with both sides opened, a fixing ring of a circular shape that is encased by one end side of the cover, the one end side being formed by folding back the cover, and a rubber ring that is encased by the other end side of the cover. When the headphone cover is attached to the headphone, the fixing ring of the cover is inserted into the ear pad of the headphone main body while being pushed and contracted by the finger, and the finger is released in the ear pad.

Then, the fixing ring is restored to a circular shape and comes into close contact with the inner back wall of the ear pad. Thereafter, the cover is attached so as to encase the ear pad.

Patent Literature 1: JP 2015-133609 A
Patent Literature 2: JP H06-44290 U

SUMMARY OF INVENTION

Technical Problem

There are various sizes of ear pads of headphones, and it is common to prepare different types of headphone covers according to their sizes. However, the headphone cover described in Patent Literature 2 cannot be attached to a headphone in which the inner diameter of the ear pad is larger than the diameter of the fixing ring in a restored state. In addition, the headphone cover cannot be attached to a headphone having an inner diameter of the ear pad smaller than a minimum size at which the fixing ring can be strongly pushed and contracted by a finger. Therefore, the headphone cover described in Patent Literature 2 has a certain limitation on the size of the headphone to which the headphone cover can be applied, and there is a problem in that it is necessary to prepare a large number of headphone covers in accordance with headphones of various sizes.

That is, when the diameter of the fixing ring is considerably increased, the fixing ring can be attached to a headphone having a considerably large size. However, in this case, when the fixing ring is to be worn on a headphone having a small size, the fixing ring cannot be inserted into the ear pad unless the fixing ring is strongly pushed and contracted by the finger, and thus it is difficult to wear the fixing ring easily. When the diameter of the fixing ring is large and the elastic force is strong, a case occurs where the fixing ring cannot be inserted into the ear pad of the headphone having a small size. If the diameter of the fixing ring is made small to some extent, the fixing ring can be attached to a headphone having a small size, but conversely, the fixing ring cannot be used on a headphone having a large size.

The present invention has been made to solve such a problem, and an object of the present invention is to enable a headphone cover configured to maintain an ear pad of a headphone in a state having a recessed space using a fastener to be used on as many sizes of headphones as possible.

Solution to Problem

In order to solve the above problem, a headphone cover of the present invention includes a fabric for covering an ear pad from an outer peripheral surface to an inner peripheral surface thereof, an elastic body for fixing an opening peripheral edge portion corresponding to a peripheral edge of an opening of the fabric to the outer peripheral surface of the ear pad or the outer peripheral surface of a housing, and a fixing member for fixing a part of the fabric to the inner peripheral surface of the ear pad or the vicinity of the inner peripheral surface, the fixing member being disposed in a recessed space formed inside the ear pad. The fixing member is a belt-like member having flexibility, and includes a plurality of first locking portions formed on one surface of the belt-like member, a second locking portion formed on the other surface on the opposite side and locked to any one of the plurality of first locking portions, and a holding portion for slidably holding the belt-like member. Then, the first locking portion and the second locking portion are formed in a shape in which the belt-like member is slidable only in one direction in which the length from the end portion of the belt-like member in the longitudinal direction to a portion held by the holding portion is shortened in a state in which the portion of the belt-like member is held by the holding portion.

Advantageous Effects of Invention

According to the present invention configured as described above, the ear pad is covered with the fabric from the outer peripheral surface to the inner peripheral surface of the ear pad in a state in which the opening peripheral edge portion of the fabric is fixed to the outer peripheral surface of the ear pad or the outer peripheral surface of the housing, and a part of the fabric is fixed to the inner peripheral surface of the ear pad or its vicinity with the fixing member. Accordingly, even when the ear pad is covered with the fabric of the headphone cover, the recessed space formed in the middle portion of the ear pad can be prevented from being blocked by the fabric of the headphone cover.

When a part of the fabric is fixed to the inner peripheral surface of the ear pad or the vicinity of the inner peripheral surface by the fixing member, the belt-like member is bent into a ring shape to hold a portion of the belt-like member by the holding portion, and the diameter of the ring is increased by sliding the belt-like member in one direction in the recessed space of the ear pad, so that the part of the fabric is fixed to the inner peripheral surface of the ear pad or the vicinity of the inner peripheral surface. Since the belt-like member slides only in one direction and does not return to the side where the diameter of the ring decreases, a part of the fabric can be stably fixed to the inner peripheral surface of the ear pad or the vicinity of the inner peripheral surface.

Since the fixing member of the present invention does not fix the fabric to the inner peripheral surface of the ear pad or the vicinity of the inner peripheral surface using the restoring force when the circular ring having an elastic force is pushed and contracted, even if the length of the belt-like member is made long such that it can be used for a headphone having a large size, it is not necessary to push and contract the ring with a strong force, and the fixing member can be used for a headphone having a small size. As a result, the headphone cover of the present invention enabled to maintain the ear pad of the headphone in a state having a recessed space using the fixing member can be used on as many sizes of headphones as

DESCRIPTION OF EMBODIMENTS

Figure 1:
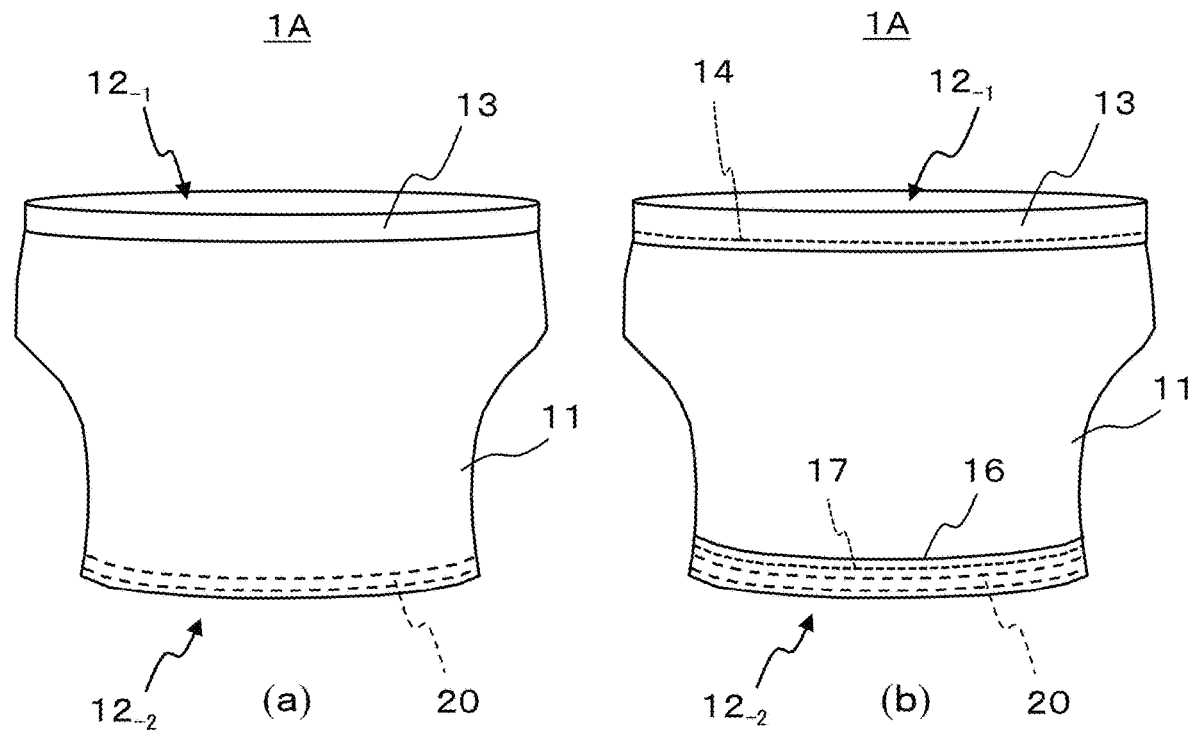
FIG. 1 is a diagram illustrating a configuration example of a headphone cover according to the present embodiment.
Figure 1:
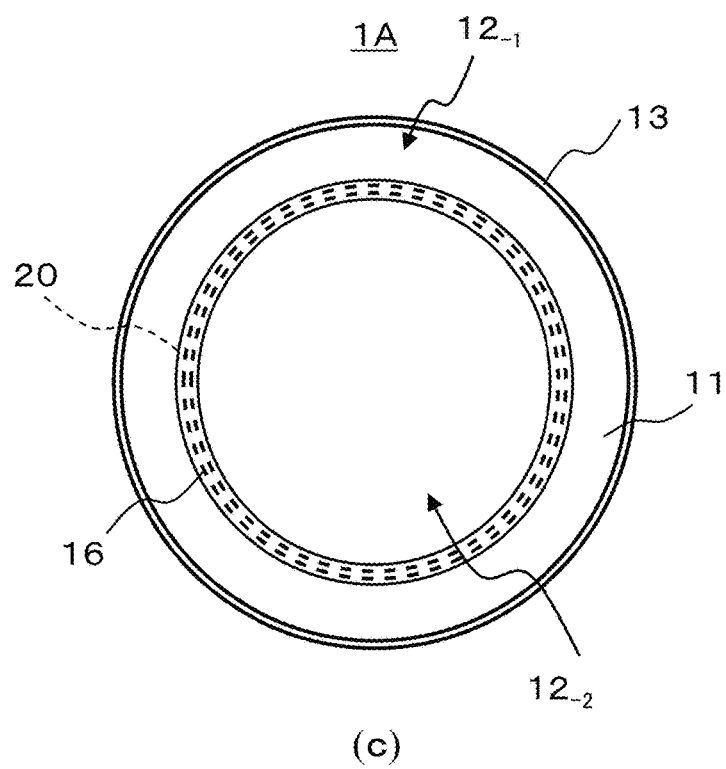

A headphone cover according to an embodiment of the present invention will be described with reference to the accompanying drawings. FIG. 1 is a diagram illustrating a configuration example of a headphone cover 1A according to the first embodiment, with (a) illustrating the obverse of an obverse surface, (b) illustrating the reverse of the obverse surface, and (c) illustrating an upper surface. The headphone cover 1A according to the present embodiment has elasticity and is deformable. FIG. 1 illustrates one aspect of the shape of the headphone cover 1A in a steady state in which no external force is applied.

As will be described later with reference to FIG. 2, the headphone cover 1A according to the present embodiment is used which being fitted on an ear pad 101 of an around ear type headphones 100. Since the ear pad 101 is formed in a ring shape, a central portion of the around ear type headphone 100 is recessed, and a cylindrical recessed space 105 is formed in the space.

As illustrated in FIG. 1, the headphone cover 1A according to the present embodiment includes a fabric 11 for covering the ear pad 101 from its outer peripheral surface to its inner peripheral surface when the headphone cover 1A is attached to the headphone 100. Openings $12_{-1}$ and $12_{-2}$ are formed at predetermined positions on the fabric 11.

In the embodiment, the fabric 11 is formed in a tubular shape, and the first opening $12_{-1}$ is formed in one end of the tubular shape while the second opening $12_{-2}$ is formed in the other end of the tubular shape. Both of the two openings $12_{-1}$ and $12_{-2}$ are formed in a circular shape, and the second opening $12_{-2}$ is formed to have a smaller diameter than the first opening $12_{-1}$.

Here, the diameter of the first opening $12_{-1}$ is substantially the same as or larger than the diameter (hereinafter, referred to as an outer diameter of the headphone 100) of a circle formed by the outer peripheral surface of the ear pad 101 or the outer peripheral surface of a housing 102 (in particular, a portion in contact with the ear pad 101) of the headphone 100 having the maximum size assumed as the attaching target of the headphone cover 1A. As will be described later, since the elastic body 13 is provided on the peripheral edge of the first opening $12_{-1}$, the headphone cover 1A can be attached in a state of being fitted to the outer peripheral surface of the ear pad 101 or the outer peripheral surface of the housing 102 by its elastic force. When the stretchable fabric 11 is used, the diameter of the first opening $12_{-1}$ may be smaller than the outer diameter of the headphone 100.

Figure 2:
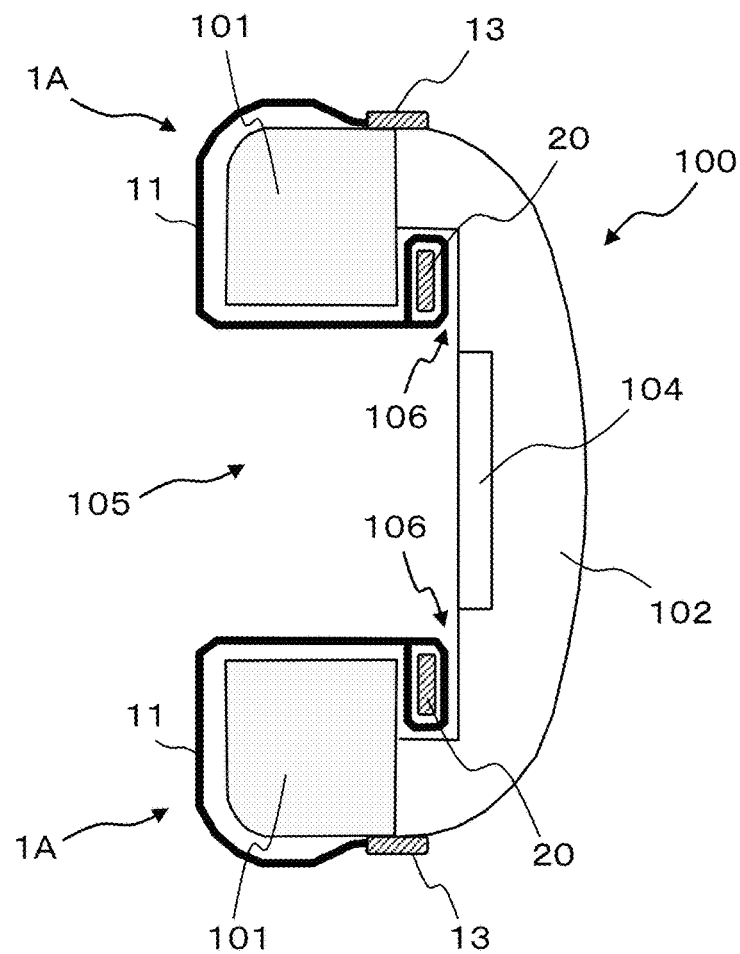
FIG. 2 is a schematic diagram illustrating a state in which the headphone covers according to the present embodiment are attached to the headphone.

In order to simplify the description below, as illustrated in FIG. 2, the headphone 100 to which the headphone cover 1A is attached is configured such that the outer peripheral surface of the ear pad 101 is flush with the outer peripheral surface of the portion of the housing 102 which is in contact with the ear pad 101 so as to be continuous with each other, and the diameter of the circle formed by the outer peripheral surface of the ear pad 101 is the same as the diameter of the circle formed by the outer peripheral surface of the portion of the housing 102 which is in contact with the ear pad 101.

Assume the outer peripheral surface of the ear pad 101 and the outer peripheral surface of the portion of the housing 102 which in contact with the ear pad 101 are discontinuous, and the diameter of the circle formed by the outer peripheral surface of the portion of the housing 102 which is in contact with the ear pad 101 is smaller than the diameter of the circle formed by the outer peripheral surface of the ear pad 101. In this case, the diameter of the first opening $12_{-1}$ is preferably larger than the diameter of the outer peripheral surface of the ear pad 101.

Furthermore, the diameter of a second opening $12_{-2}$ is substantially the same as or larger than the diameter (hereinafter, referred to as an inner diameter of the headphone 100) of a circle formed by the inner peripheral surface of the ear pad 101 of the headphone 100 having the maximum size assumed as the attaching target of the headphone cover 1A. When the stretchable fabric 11 is used, the diameter of the second opening $12_{-2}$ may be smaller than the inner diameter of the headphone 100.

It is preferable that the headphone cover 1A of the present embodiment can be used for the headphone 100 of various sizes by using the fabric 11 having high elasticity.

An elastic body 13 is provided at a first opening peripheral edge portion corresponding to the peripheral edge of the first opening $12_{-1}$. The elastic body 13 is for fixing the first opening peripheral edge portion of the fabric 11 to the outer peripheral surface of the ear pad 101 or the outer peripheral surface of the housing 102 when the headphone cover 1A is attached to the headphones 100.

The elastic body 13 is formed into a ring shape, and the diameter of the ring in a state of not being extended is smaller than the outer diameter of the headphone 100 having the minimum size assumed as the attaching target of the headphone cover 1A. In addition, the diameter of the ring of the elastic body 13 in a state of being extended is larger than the outer diameter of the headphone 100 having the maximum size assumed as the attaching target of the headphone cover 1A. Accordingly, the first opening peripheral edge portion of the fabric 11 is fixed to the outer peripheral surface of the ear pad 101 or the outer peripheral surface of the housing 102 with a force that causes the elastic body 13 to contract to the original state by extending the elastic body 13 and hooking it on the outer peripheral surface of the ear pad 101 or the outer peripheral surface of the housing 102.

In the present embodiment, elastic webbing is used as an example of the elastic body 13 (to be referred to as the elastic webbing 13 hereinafter). More specifically, the elastic webbing 13 is sewn to the fabric 11 of the first opening peripheral edge portion of the first opening $12_{-1}$ with a thread 14. The thread 14 used here preferably has stretchability. Furthermore, the length of a yarn 14 is preferably set to be longer than the length of the entire circumference of an elastic webbing 13 in the most contracted state (the length of the circumference of the elastic webbing 13 in the steady state illustrated in FIG. 1). The elastic webbing 13 is used because it can be sewn to the fabric 11 easily as compared with round rubber.

A bag-shaped portion 16 is provided at a second opening peripheral edge portion corresponding to a peripheral edge of the second opening $12_{-2}$ (in FIG. 1(c), the bag-shaped portion 16 is schematically deformed). As illustrated in FIG. 1(b), the bag-shaped portion 16 is formed by folding back the second opening peripheral edge portion of the fabric 11 from the obverse side to the reverse side over the entire circumference and sewing the side close to the front end of the folded portion with a yarn 17.

Figure 3:
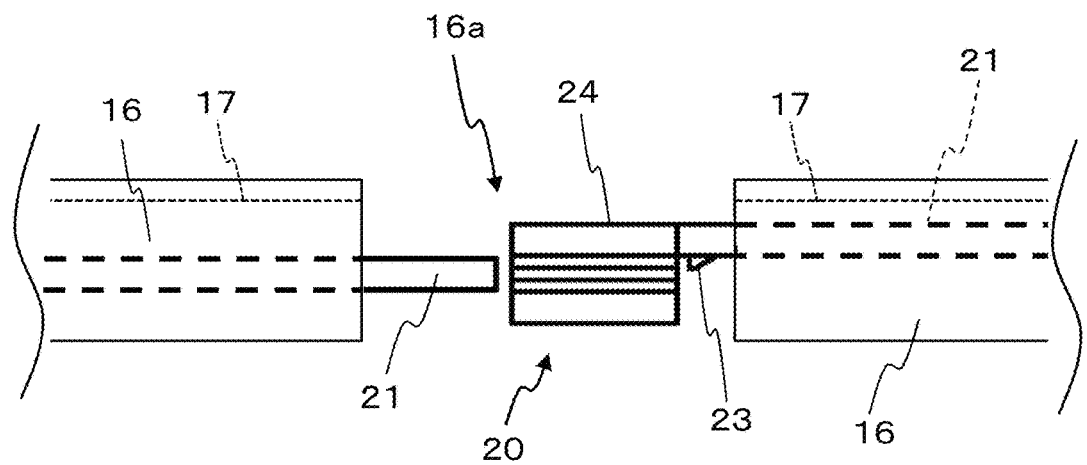
FIG. 3 is a diagram illustrating a chipped portion provided in a bag-shaped portion.

As illustrated in FIG. 3, a chipped portion 16a is provided in a part of the bag-shaped portion 16, and a fixing member (fastener) 20 is inserted and embedded in the bag-shaped portion 16 from the chipped portion 16a.

When the headphone cover 1A is attached to the headphone 100, the fixing member 20 is disposed in the recessed space 105 formed inside the ear pad 101 to fix a part of the fabric 11 to the inner peripheral surface of the ear pad 101 or the vicinity of the inner peripheral surface (hereinafter, it may be referred to as an inner peripheral surface or the like). In the present embodiment, the part of the fabric 11 is the second opening peripheral edge portion of the second opening $12_{-2}$.

As an example, the fixing member 20 is a belt-like member made of resin having flexibility, and can be formed into a ring shape by being bent. In the present specification, the term "belt shape" is a shape in which a certain width is elongated and both ends are present in the longitudinal direction. In the present embodiment, in particular, a belt-like member is used which is linearly elongated with a constant width and a constant thickness and has elongated flat surfaces facing each other. As will be described in detail later, the fixing member 20 can be fixed by adjusting a diameter of a ring formed by bending the belt-like member. The fixing member 20 can be deformed from the ring state narrowed inward to the ring state expanded outward by adjusting the diameter of the ring.

For example, as illustrated in FIG. 3, both ends of the fixing member 20 formed into a ring shape inserted into the bag-shaped portion 16 can be exposed from the chipped portion 16a, and the user can adjust the size of the diameter of the fixing member 20 formed into a ring shape by holding and sliding the portions of both ends of the fixing member 20 by hand. As a result, the headphone cover 1A according to the present embodiment can be used for the headphone 100 having various sizes with the cylindrical recessed spaces 105 having different diameters.

The fixing member 20 of the present embodiment is formed into a ring shape in the bag-shaped portion 16 formed in a part (second opening peripheral edge portion) of the fabric 11, and guides a part (second opening peripheral edge portion) of the fabric 11 to the inner peripheral surface of the ear pad 101 or the reverse surface of the ear pad 101 positioned in the vicinity of the inner peripheral surface by expanding the diameter of the ring from the smaller side to the larger side. Then, in a state in which the second opening peripheral edge portion comes into contact with the inner peripheral surface or the like of the ear pad 101, such a state can be maintained.

Instead of sewing the elastic webbing 13 to the first opening peripheral edge portion of the fabric 11, the first opening peripheral edge portion may also constitute a bag-shaped portion in the same manner as the bag-shaped portion 16, and a round rubber or an elastic webbing may be embedded in the bag-shaped portion. In addition, the fabric 11 may be made of a material having an elastic force so as not to provide an elastic body such as elastic webbing 13 at the first opening peripheral edge portion. In this case, the elastic force of the opening peripheral edge portion may be increased by folding back and sewing the first opening peripheral edge portion doubly or more.

FIG. 2 is a schematic diagram illustrating a state in which the headphone cover 1A configured as described above is attached to the headphones 100. FIG. 2 illustrates a cross section of one headphone unit of the headphone 100 including the headband and the pair of headphone units and the headphone cover 1A attached to the headphone unit as a simple schematic diagram.

As described above, in the case of the around ear type headphone 100, the middle portion of the ring-shaped ear pad 101 is recessed, and the cylindrical recessed space 105 is formed in the middle portion. The loudspeaker unit 104 exists at the bottom portion of the recessed space 105. In addition, a gap 106 is formed between the reverse surface of the ear pad 101 and the housing 102 exists at the bottom portion of the inner peripheral surface of the ear pad 101.

The fixing member 20 is sized to fit in the gap 106 and fixes the second opening peripheral edge portion of the fabric 11 to near the inner peripheral surface of the ear pad 101 inside the gap 106. Here, as long as the headphone 100 is formed to have a size such that the inner diameter (=the diameter of inner peripheral surface of the ear pad 101) of the gap 106 formed into a ring shape is smaller than the maximum diameter that can be adjusted by forming the fixing member 20 into a ring shape, even the headphone 100 having a different size and shape can fix the second opening peripheral edge portion of the fabric 11 to the vicinity of the inner peripheral surface of the ear pad 101 in a state in which the fixing member 20 is placed in the gap 106.

Since the ear pad 101 is made of a cushion material having an elastic force, the fixing member 20 can be inserted into the gap 106 even if the fixing member 20 is actually formed to be slightly thicker than the gap 106. When the fixing member 20 is configured to have such a size, it is possible to make the fixing member 20 inserted into the gap 106 less likely to come off by receiving pressure or frictional force from the reverse surface of the ear pad 101.

When the headphone cover 1A is attached to the headphone 100, for example, the fixing member 20 (the second opening peripheral edge portion of the fabric 11) is inserted into the gap 106 over the entire circumference while deforming (increasing the diameter of the ring) the fixing member 20 formed into a ring shape and embedded in the bag-shaped portion 16 formed in the second opening peripheral edge portion of the fabric 11 in a state in which the reverse surface of the headphone cover 1A comes on the outer side (a state in which the reverse surface is visible from the outside), as illustrated in FIG. 1(b).

Next, the inner peripheral surface and the outer peripheral surface of the ear pad 101 are sequentially covered with the fabric 11 while the fabric 11 is reversed such that the surface of the fabric 11 can be seen from the outside. And then, hooking the elastic webbing 13 sewn to the first opening peripheral edge portion of the fabric 11 on the outer peripheral surface of the ear pad 101 or the housing 102 fixes the first opening peripheral edge portion of the fabric 11 to the outer peripheral surface of the ear pad 101 or the housing 102.

Note that it is also possible to attach the headphone cover 1A in a reverse procedure. That is, hooking the elastic webbing 13 sewn to the first opening peripheral edge portion of the fabric 11 on the outer peripheral surface of the ear pad 101 or the housing 102 fixes the first opening peripheral edge portion of the fabric 11 to the outer peripheral surface of the ear pad 101 or the housing 102 in a state in which the surface of the headphone cover 1A is placed outside (seen from outside), as illustrated in FIG. 1(a).

Next, the outer peripheral surface and the inner peripheral surface of the ear pad 101 are sequentially covered with the fabric 11, and the fixing member 20 (the second opening peripheral edge portion of the fabric 11) is inserted into the gap 106 over the entire circumference while the fixing member 20 formed into a ring shape and embedded in the bag-shaped portion 16 formed in the second opening peripheral edge portion of the fabric 11 is deformed.

As described above, the first opening peripheral edge portion of the fabric 11 is fixed to the outer peripheral surface of the ear pad 101 or the housing 102 by the elastic webbing 13, and the second opening peripheral edge portion of the fabric 11 is fixed to the vicinity of the inner peripheral surface of the ear pad 101 by the fixing member 20 in the gap 106 formed in the bottom portion of the inner peripheral surface of the ear pad 101 (between the reverse surface of the ear pad 101 and the housing 102). In this state, the outer peripheral surface and the inner peripheral surface of the ear pad 101 are covered with the fabric 11. In FIG. 2, the fabric 11 is illustrated in a state of being separated from the ear pad 101 for easy understanding of appearance, but in practice, the fabric 11 can be fitted from the outer peripheral surface to the inner peripheral surface of the ear pad 101.

In this way, even when the ear pad 101 is covered with the fabric 11 of the headphone cover 1A, the cylindrical recessed space 105 formed in the middle portion of the ear pad 101 can be prevented from being blocked by the fabric 11 of the headphone cover 1A. This enables the user to use an around ear type headphone 100 attached with the headphone cover 1A according to the present embodiment with a sense of use similar to that of an around ear type.

Figure 4:
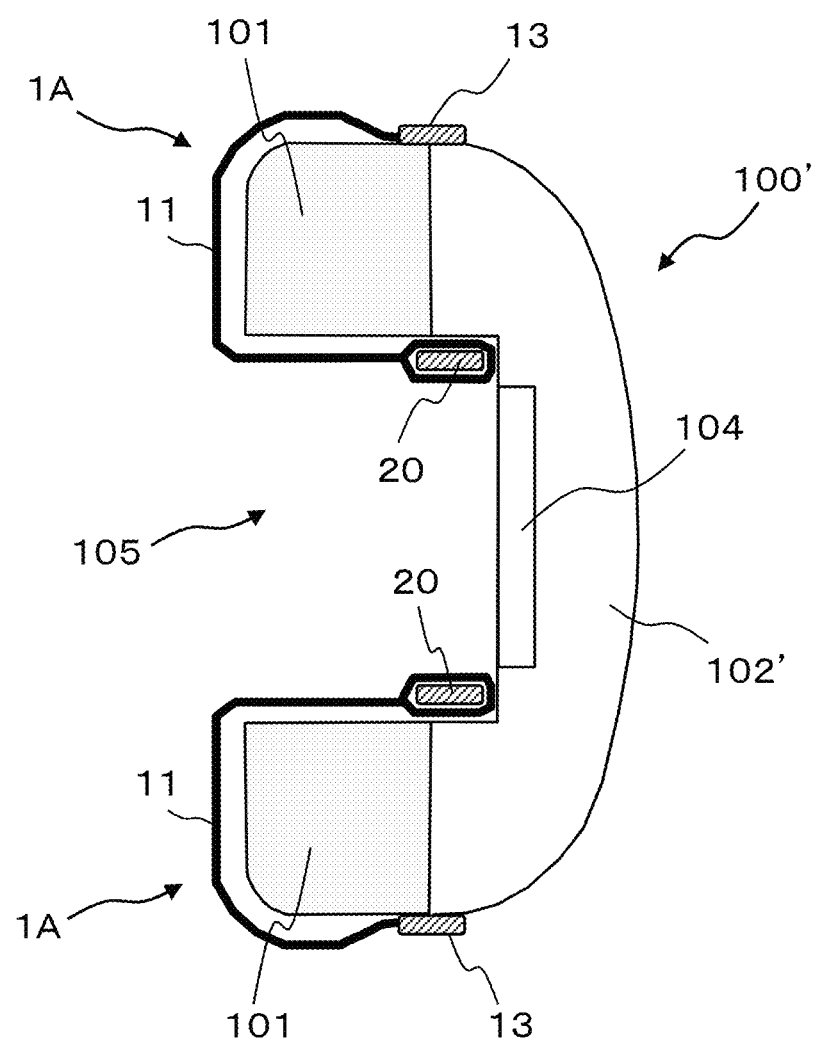
FIG. 4 is a diagram illustrating a state in which the headphone covers according to the present embodiment are attached to another type of headphone.

FIG. 4 is a diagram illustrating a state in which the headphone covers 1A according to the present embodiment are attached to another type of headphone 100'. FIG. 4 illustrates a state in which the headphone cover 1A is attached to the headphone 100' of a type having no gap at a bottom portion of the inner peripheral surface of the ear pad 101. In this case, the second opening peripheral edge portion of the fabric 11 is fixed to the bottom portion of the inner peripheral surface of the ear pad 101 or the inner peripheral surface of a housing 102' with the fixing member 20, and the ear pad 101 is covered with the fabric 11.

In this case, as long as the headphone 100' is formed to have a size such that the diameter of the inner peripheral surface of the ear pad 101 is smaller than the maximum diameter that can be adjusted by forming the fixing member 20 into a ring shape, even the headphone 100' having a different size and shape can fix the second opening peripheral edge portion of the fabric 11 to the inner peripheral surface of the ear pad 101 in a state in which the fixing member 20 is pressed against the inner peripheral surface of the ear pad 101.

Figure 5:
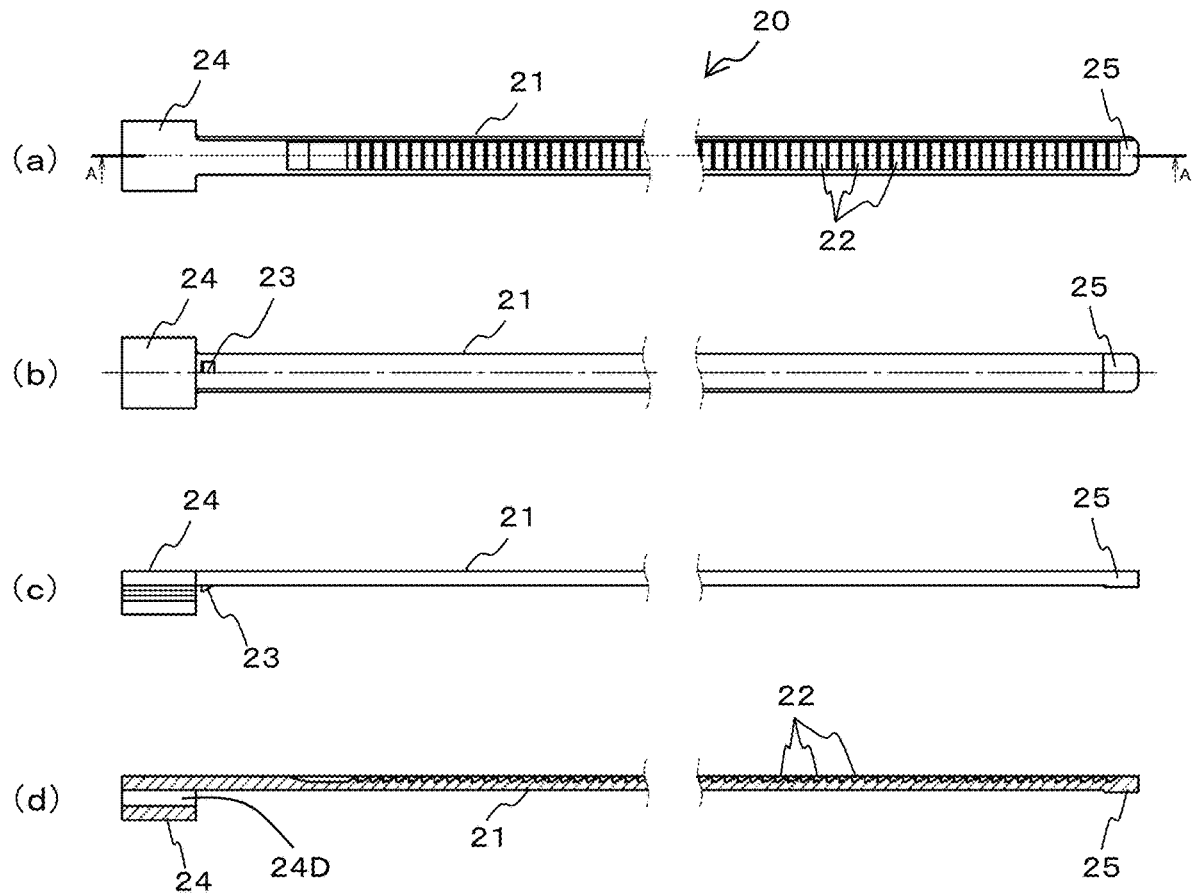
FIG. 5 is a diagram illustrating a configuration example of a fixing member according to the present embodiment.

FIG. 5 is a diagram showing a configuration example of the fixing member 20, where FIG. 5(a) shows an upper surface view (plan view), FIG. 5(b) shows a lower surface view (bottom surface view), FIG. 5(c) shows a front view, and FIG. 5(d) shows a cross-sectional view taken along line A-A. As described above, the fixing member 20 is formed of the belt-like member 21 having flexibility.

A plurality of first locking portions 22 is formed on an upper surface (corresponding to "one surface" in the claims) of the belt-like member 21. The plurality of first locking portions 22 is disposed along the longitudinal direction of the belt-like member 21 except for a portion having a predetermined length from one end (an end portion provided with a holding portion 24 to be described later) of the belt-like member 21 and a terminal end portion 25 having a predetermined length from the other end of the belt-like member 21. In the following description, an end portion at which the holding portion 24 is provided is defined as a front end of the belt-like member 21, and an end portion on the opposite side is defined as a rear end.

Figure 6:
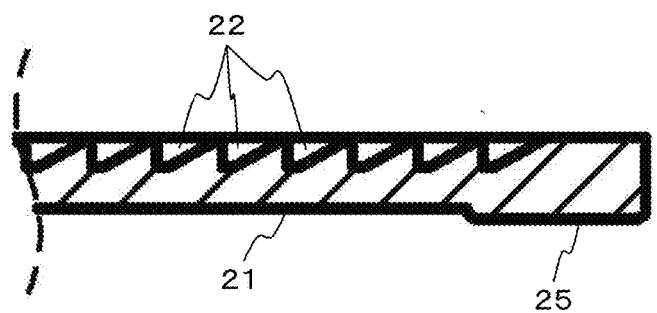
FIG. 6 is an enlarged diagram of a first locking portion.

As illustrated in FIG. 6 in which a part of FIGS. 5(a) and 5(d) is enlarged, each of the first locking portions 22 is a concave portion having a right triangular cross section when viewed from the front direction and having a rectangular vertical surface and a rectangular inclined surface. The plurality of first locking portions 22 is continuously disposed in the same direction to be formed in a saw-tooth shape as a whole. Continuous means that two adjacent first locking portions 22 are disposed without a gap.

Note that although FIG. 5 illustrates the configuration in which the plurality of first locking portions 22 is continuously disposed, the plurality of first locking portions 22 may be intermittently (discretely) disposed. As described later, the plurality of first locking portions 22 has a function of adjusting a diameter when the belt-like member 21 is bent into a ring shape. Therefore, it is preferable to continuously dispose the plurality of first locking portions 22 from the viewpoint that the diameter of the ring can be finely adjusted.

A second locking portion 23 that is in a locked state with any of the plurality of first locking portions 22 is formed on a lower surface (corresponding to "the other surface opposite to the one surface" in the claims) of the belt-like member 21. The second locking portion 23 is disposed on the lower surface of the belt-like member 21 at a portion not facing the first locking portion 22. Specifically, the second locking portion 23 is disposed at a position in the vicinity of the holding portion 24 on the rear end side of the holding portion 24 provided at the front end of the belt-like member 21.

Figure 7:
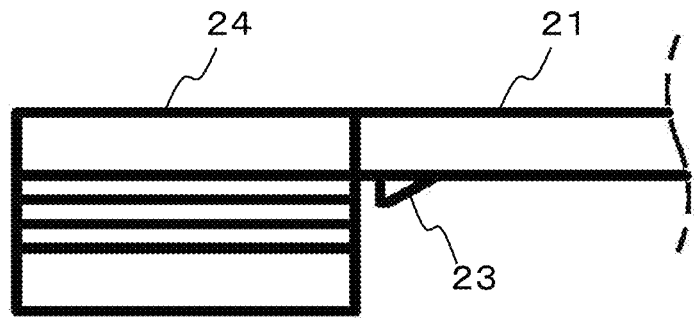
FIG. 7 is an enlarged diagram of a second locking portion.

As illustrated in FIG. 7 in which a part of FIGS. 5(b) and 5(c) is enlarged, the second locking portion 23 is a convex portion having a right triangular cross section when viewed from the front direction and having a rectangular vertical surface and a rectangular inclined surface. The convex shape of the second locking portion 23 is substantially the same shape and size as the concave shape of the first locking portion 22. As a result, any one of the plurality of first locking portions 22 and the second locking portion 23 are fitted to each other. In the fitted state, the second locking portion 23 is slidable along the inclined surface in a direction in which the vertical surface thereof is separated from the vertical surface of the first locking portion 22, but vertical surfaces collide with each other in the opposite direction and enter a non-slidable locking state.

As described above, the holding portion 24 is provided at one end (front end) of the belt-like member 21 in the longitudinal direction. The holding portion 24 is configured to slidably hold a portion other than the front end of the belt-like member 21. That is, as schematically illustrated in FIG. 8, the belt-like member 21 is bent into a ring shape, and the holding portion 24 slidably holds the portion of the belt-like member 21 where the first locking portion 22 is provided in a state in which the belt-like member 21 is inserted into an internal space 24D (see FIG. 5(d)) of the holding portion 24 from the rear end thereof, so that the belt-like member 21 can be maintained in a ring-shaped bent state.

Figure 8:
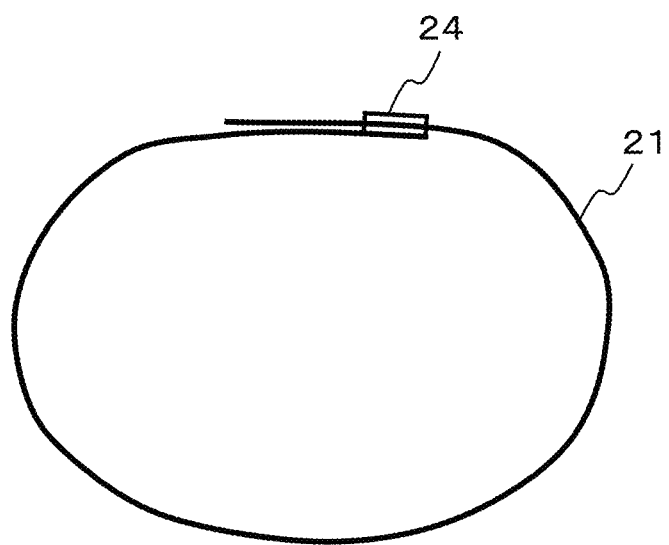
FIG. 8 is a schematic diagram illustrating a state in which a belt-like member is formed into a ring shape.

Note that FIG. 8 illustrates a state in which the belt-like member 21 is bent such that the upper surface (the surface on the side on which the first locking portion 22 is provided) of the belt-like member 21 faces the inside of the ring and the lower surface (the surface on the side on which the second locking portion 23 is provided) of the belt-like member 21 faces the outside of the ring, but it is also possible to bend the belt-like member in the opposite direction. That is, the belt-like member 21 can be bent such that the upper surface of the belt-like member 21 faces the outside of the ring and the lower surface of the belt-like member 21 faces the inside of the ring.

Figure 9:
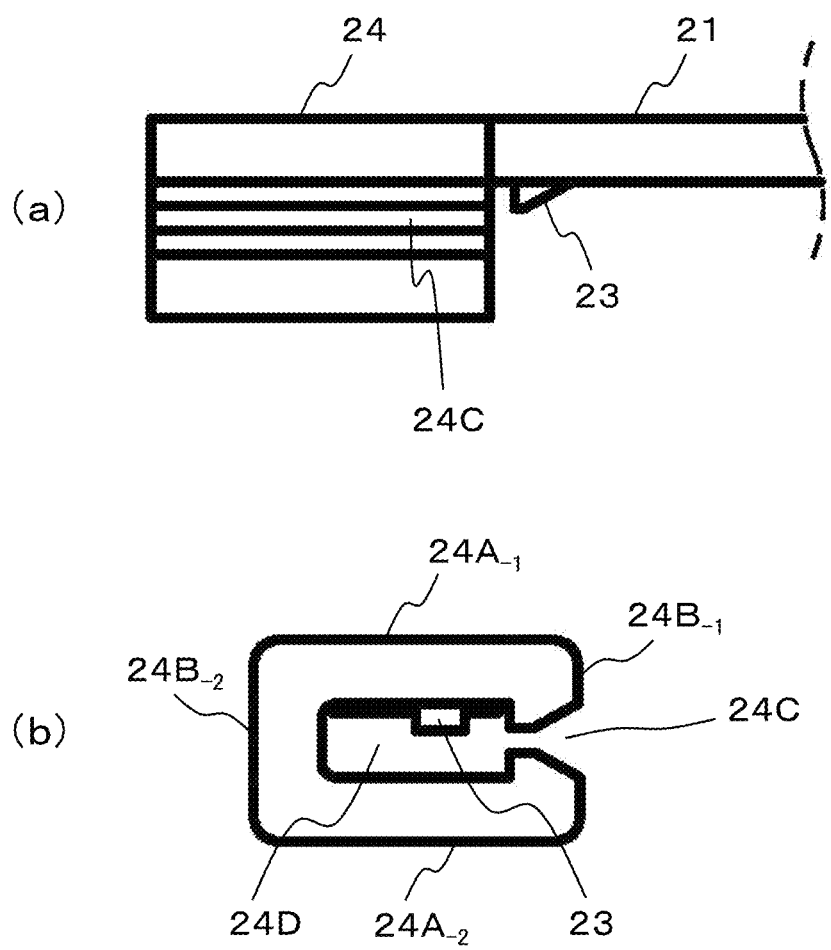
FIG. 9 is an enlarged diagram of a holding portion.

The first locking portion 22 and the second locking portion 23 are formed in a shape in which the belt-like member 21 is slidable only in one direction in which the length (length of a portion where the belt-like member 21 formed into a ring shape protrudes from the holding portion 24) from the rear end of the belt-like member 21 in the longitudinal direction to a portion held by the holding portion 24 is shortened in a state in which the portion of the belt-like member 21 is held by the holding portion 24. The one direction in which the length of the portion where the belt-like member 21 formed into a ring shape protrudes from the holding portion 24 is shortened is a direction in which the diameter of the ring formed by the belt-like member 21 is increased FIG. 9 is a diagram illustrating the enlarged holding portion 24, in which FIG. 9(a) is a front view and FIG. 9 (b) is a side view. As illustrated in FIG. 9, the holding portion 24 has a pair of upper and lower clamping surfaces $24A_{-1}$ and $24A_{-2}$ that clamp the belt-like member 21 from the directions of the upper surface and the lower surface, and a pair of width clamping surfaces $24B_{-1}$ and $24B_{-2}$ that clamp the belt-like member 21 from the width direction. These four clamping surfaces $24A_{-1}$, $24A_{-2}$, $24B_{-1}$, and $24B_{-2}$ form the internal space 24D through which the belt-like member 21 is insertable in a direction parallel to the longitudinal direction of the belt-like member 21. That is, the holding portion 24 is provided in parallel to the belt-like member 21.

The pair of upper and lower clamping surfaces $24A_{-1}$ and $24A_{-2}$ are rectangular planes, and one side (the side in the direction perpendicular to the longitudinal direction of the belt-like member 21 to be inserted into the internal space 24D) of the inner surface forming the internal space 24D has a length substantially equal to or slightly larger than the width of the belt-like member 21. The pair of width clamping surfaces $24B_{-1}$ and $24B_{-2}$ (one width clamping surface $24B_{-1}$ is a surface when it is assumed that there is no slit 24C described below) are rectangular planes, and one side (the side in the direction perpendicular to the longitudinal direction of the belt-like member 21) of the inner surface forming the internal space 24D has a length substantially equal to or slightly larger than the thickness of the belt-like member 21. As a result, the cross-sectional shape of the internal space 24D is formed to be substantially the same shape and substantially the same size as the cross-sectional shape of the belt-like member 21.

Of the pair of width clamping surfaces $24B_{-1}$ and $24B_{-2}$, one width clamping surface $24B_{-1}$ is formed with a slit 24C thinner than the thickness of the belt-like member 21. The holding portion 24 is made of a flexible resin or the like, and the pair of upper and lower clamping surfaces $24A_{-1}$ and $24A_{-2}$ are rotatable in a direction of increasing the thickness of the slit 24C with the other width clamping surface $24B_{-2}$ of the pair of width clamping surfaces $24B_{-1}$ $24B_{-2}$ as a base point.

As a result, when the belt-like member 21 slides in the internal space 24D of the holding portion 24 to change the position of the first locking portion 22 to be engaged with the second locking portion 23, the pair of upper and lower clamping surfaces $24A_{-1}$ and $24A_{-2}$ rotates, so that the belt-like member 21 can move up and down in the internal space 24D. Therefore, it is not necessary to provide a mechanism for moving the second locking portion 23 up and down, and the fixing member 20 can be made compact.

Figure 10:
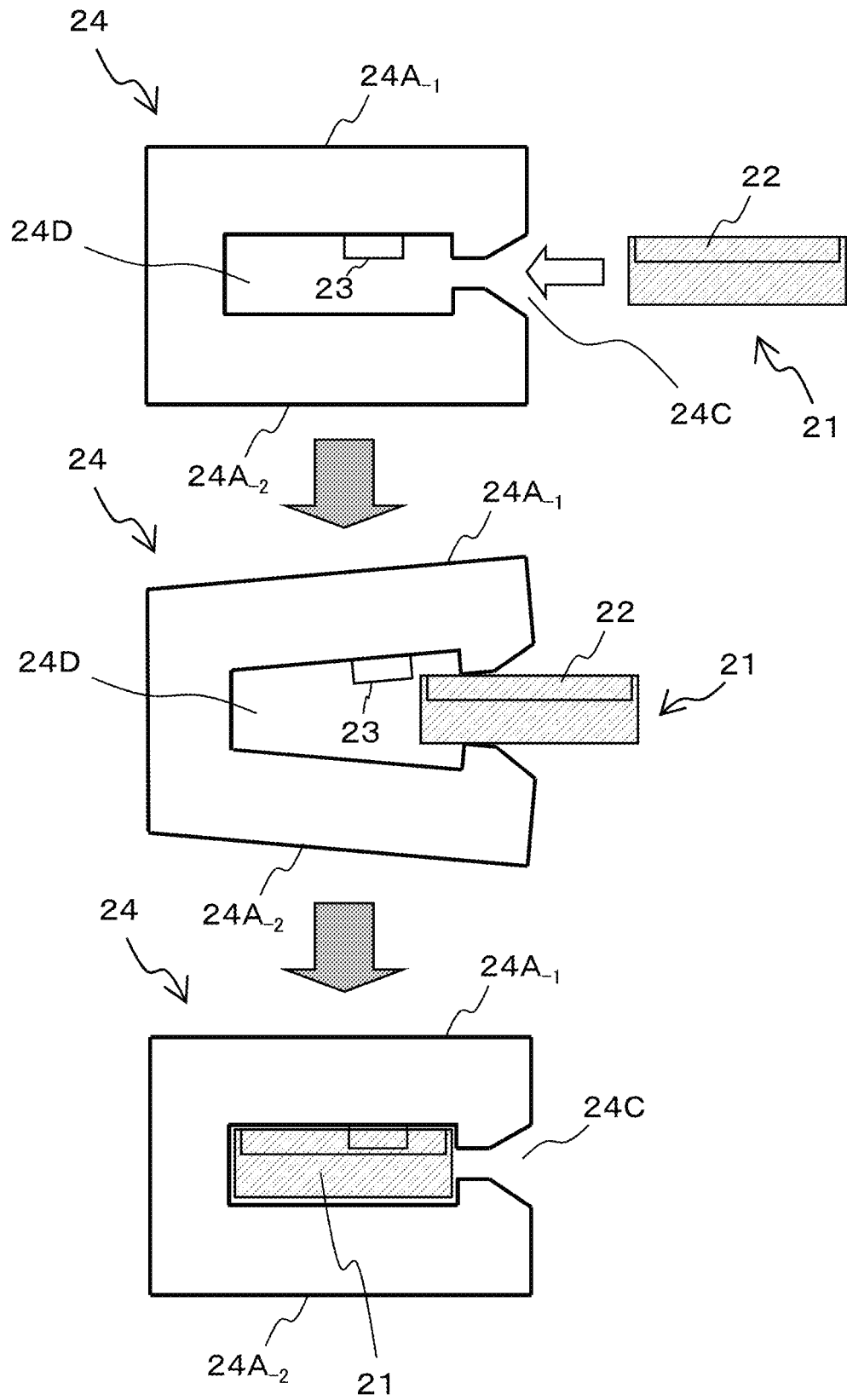
FIG. 10 is a diagram illustrating a state in which the belt-like member is inserted into the internal space of the holding portion from a slit.

In the present embodiment, as shown in FIG. 10, a portion of the belt-like member 21 is configured to be slidable from the slit 24C and insertable into the internal space 24D of the holding portion 24. As illustrated in FIG. 9(b), the slit 24C is formed so as to be wider on the outer side and narrower on the inner side of one width clamping surface $24B_{-1}$. Therefore, the opposing edge surfaces of the slit 24C are tapered surfaces inclined such that the separation distance gradually decreases from the outer side of the holding portion 24 toward the inner side (internal space 24D side). As a result, it is possible to facilitate the work of sliding and inserting a portion of the belt-like member 21 into the internal space 24D from the outside of the holding portion 24 through the slit 24C.

As described above, in a state in which the belt-like member 21 is inserted from the slit 24C into the internal space 24D and a portion of the belt-like member 21 is held by the holding portion 24, the belt-like member 21 is slidable only in one direction in which the diameter of the ring increases. On the other hand, when a portion of the belt-like member 21 is not held by the holding portion 24, the ring formed by the belt-like member 21 can be freely contracted in a direction of decreasing the diameter. Therefore, the second opening peripheral edge portion of the fabric 11 can be fixed to the inner peripheral surface or the like of the ear pad 101 by the fixing member 20 by the following procedure.

First, the belt-like member 21 is inserted into the bag-shaped portion 16 of the fabric 11. At this time, the holding portion 24 at the front end of the belt-like member 21 and a portion having an arbitrary length from the rear end of the belt-like member 21 are brought out of the bag-shaped portion 16 from the chipped portion 16a of the bag-shaped portion 16. Next, in a state in which the belt-like member 21 is not inserted into the internal space 24D of the holding portion 24, the diameter of the ring formed by bending the belt-like member 21 is adjusted to be smaller than the diameter of the circle formed by the inner peripheral surface of the ear pad 101.

Then, in this state, the belt-like member 21 is inserted into the internal space 24D of the holding portion 24 from the slit 24C. As a result, the first locking portion 22 at any position and the second locking portion 23 are locked, and a ring state having the small diameter can be maintained. In this way, the fixing member 20 formed into a ring shape in the bag-shaped portion 16 of the fabric 11 can be put into the recessed space 105 of the ear pad 101.

Thereafter, in the recessed space 105 of the ear pad 101, the belt-like member 21 is slid in a direction of expanding the diameter of the ring until the second opening peripheral edge portion of the fabric 11 comes into contact with the inner peripheral surface or the like of the ear pad 101, and the first locking portion 22 at a different position and the second locking portion 23 are locked. As a result, it is possible to maintain a ring state with a large diameter and fix the second opening peripheral edge portion of the fabric 11 to the inner peripheral surface or the like of the ear pad 101.

As shown in FIG. 9(b) and FIG. 5(b), the second locking portion 23 is formed on the lower surface of the belt-like member 21 at a position eccentrically located toward the slit 24C side from the center position of the belt-like member 21 in the width direction. This is a measure for facilitating sliding of the belt-like member 21 in the internal space 24D of the holding portion 24.

That is, when the belt-like member 21 slides in the internal space 24D of the holding portion 24, the first locking portion 22 needs to climb over the second locking portion 23 disposed at a position in the vicinity of the holding portion 24, and at this time, the belt-like member 21 moves up and down in the internal space 24D. Therefore, the pair of upper and lower clamping surfaces $24A_{-1}$ and $24A_{-2}$ needs to rotate by an amount necessary for the first locking portion 22 to get over the second locking portion 23. Here, by disposing the second locking portion 23 at a position as far as possible from the other width clamping surface $24B_{-2}$ serving as a base point of rotation, it is possible to reduce a necessary rotation amount (a bending amount of the holding portion 24) as much as possible. Therefore, it is possible to reduce the force required to bend the holding portion 24 when sliding the belt-like member 21 in the internal space 24D, and it is possible to easily adjust the diameter of the ring formed by the belt-like member 21.

Figure 11:
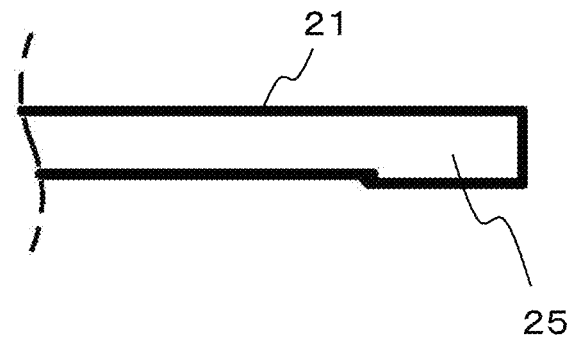
FIG. 11 is an enlarged diagram of a terminal end portion of the belt-like member.

As illustrated in FIG. 11 in which a part of FIG. 5(c) is enlarged, the terminal end portion 25 having a predetermined length including the rear end of the belt-like member 21 in the longitudinal direction is configured to be thicker than the thickness other than the terminal end portion 25. The first locking portion 22 is not provided at the terminal end portion 25. The thickness of the terminal end portion 25 is substantially the same as or slightly larger than the thickness of the internal space 24D of the holding portion 24. On the other hand, the thickness of the belt-like member 21 other than the terminal end portion 25 is slightly thinner than the thickness of the internal space 24D as described above.

As a result, when the diameter of the ring is expanded in a state in which the belt-like member 21 is held by the holding portion 24, when the portion where the first locking portion 22 is provided passes through the internal space 24D and the terminal end portion 25 enters the internal space 24D, the terminal end portion 25 comes into contact with the pair of upper and lower clamping surfaces $24A_{-1}$ and $24A_{-2}$ or is brought into pressure contact with the pair of upper and lower clamping surfaces $24A_{-1}$ and $24A_{-2}$ to generate stronger resistance than before. Therefore, the user can recognize by the feel of the hand that the diameter of the ring has been fully expanded until the terminal end portion 25 of the belt-like member 21 comes into contact with the holding portion 24.

Figure 12:
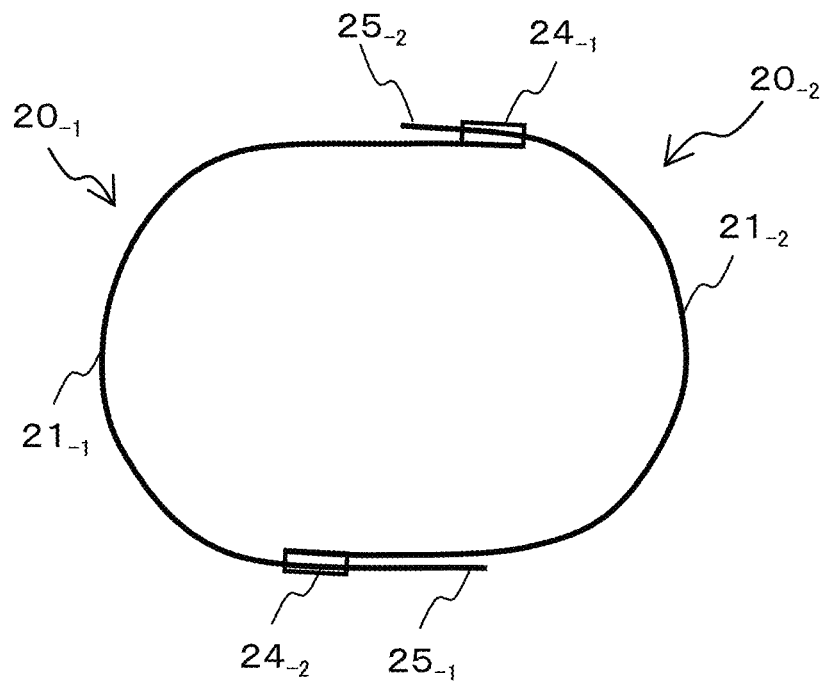
FIG. 12 is a diagram illustrating a state in which the fixing member of the present embodiment is connected and used.

As schematically illustrated in FIG. 12, the fixing member 20 of the present embodiment can also be used by connecting a plurality of fixing members 20. For example, by causing the holding portion $24_{-1}$ of a first fixing member $20_{-1}$ to hold a belt-like member $21_{-2}$ of a second fixing member $20_{-2}$ and causing a holding portion $24_{-2}$ of a second fixing member $20_{-2}$ to hold a belt-like member $21_{-1}$ of the first fixing member $20_{-1}$, it is possible to form one ring state by the two connecting fixing members $20_{-1}$ and $20_{-2}$.

In this case, for example, when the first belt-like member $21_{-1}$ is slid to expand the diameter of the ring in a state in which the belt-like members $21_{-1}$ and $21_{-2}$ are held by the holding portions $24_{-1}$ and $24_{-2}$, in a case where a first terminal end portion $25_{-1}$ comes into contact with the second holding portion $24_{-2}$, the user can recognize by the feel of the hand that the diameter of the ring has been expanded until the terminal end portion $25_{-1}$ of the first belt-like member $21_{-1}$ comes into contact with the second holding portion $24_{-2}$.

At this time, if a second terminal end portion $25_{-2}$ of the second belt-like member $21_{-2}$ has not yet come into contact with the first holding portion $24_{-1}$, the diameter of the ring can be further expanded by sliding the second belt-like member $21_{-2}$. At this time, while the first terminal end portion $25_{-1}$ comes into contact with the second holding portion $24_{-2}$ to generate strong resistance, the second belt-like member $21_{-2}$ is not in pressure contact with the first holding portion $24_{-1}$. Therefore, while preventing the first terminal end portion $25_{-1}$ from coming off from the second holding portion $24_{-2}$, the second belt-like member $21_{-2}$ can be slid to further expand the diameter of the ring.

Even after the terminal end portion 25 of the belt-like member 21 comes into contact with the holding portion 24, the belt-like member 21 can be pulled out from the holding portion 24 by sliding the belt-like member 21 with a strong force. Here, as illustrated in FIG. 11, the step portion at the boundary between the terminal end portion 25 and the other portion is a tapered surface inclined such that the thickness gradually decreases from the rear end side toward the front end side of the belt-like member 21. As a result, it is possible to easily pull out the belt-like member 21 from the holding portion 24 as compared with a case where the belt-like member does not have a tapered surface.

As described above in detail, in the present embodiment, in the headphone cover 1A configured such that the ear pad 101 is covered with the fabric 11 from the outer peripheral surface to the inner peripheral surface thereof, and a part (second opening peripheral edge portion) of the fabric 11 is fixed to the inner peripheral surface or the like of the ear pad 101 using the fixing member 20 such that the recessed space 105 formed in the middle portion of the ear pad 101 is not closed, the fixing member 20 is configured by the belt-like member 21 having flexibility, the plurality of first locking portions 22 is formed on the upper surface of the belt-like member 21, the second locking portion 23 is formed on the lower surface, and the holding portion 24 for slidably holding a portion other than the rear end of the belt-like member 21 is provided. Then, the first locking portion 22 and the second locking portion 23 are formed in a shape in which the belt-like member 21 is slidable only in one direction in which the length from the rear end of the belt-like member 21 in the longitudinal direction to a portion held by the holding portion 24 is shortened in a state in which the portion of the belt-like member 21 is held by the holding portion 24.

According to the present embodiment configured as described above, when a part of the fabric 11 is fixed to the inner peripheral surface or the like of the ear pad 101 by the fixing member 20, the belt-like member 21 is bent into a ring shape to hold a portion of the belt-like member 21 by the holding portion 24, and the diameter of the ring is increased by sliding the belt-like member 21 in one direction in the recessed space 105 of the ear pad 101, so that the part of the fabric 11 is fixed to the inner peripheral surface or the like of the ear pad 101. Since the belt-like member 21 slides only in one direction and does not return to the side where the diameter of the ring decreases, the part of the fabric 11 can be stably fixed to the inner peripheral surface or the like of the ear pad 101.

In addition, since the fixing member 20 of the present embodiment does not fix the fabric 11 to the inner peripheral surface or the like of the ear pad 101 using the restoring force when the circular ring having an elastic force is pushed and contracted, even if the length of the belt-like member 21 is made long such that it can be used for a headphone having a large size, it is not necessary to push and contract the ring with a strong force, and the fixing member can be used for a headphone having a small size. As a result, the headphone cover 1A of the present embodiment enabled to maintain the ear pad 101 of the headphone in a state having a recessed space 105 using the fixing member 20 can be used on as many sizes of headphones as possible.

Furthermore, in the present embodiment, as the configuration of the holding portion 24, the slit 24C is formed on the width clamping surface $24B_{-1}$ that is one of the pair of width clamping surfaces $24B_{-1}$ and $24B_{-2}$, and the pair of upper and lower clamping surfaces $24A_{-1}$ and $24A_{-2}$ are made rotatable with the other width clamping surface $24B_{-2}$ as a base point. As a result, a portion of the belt-like member 21 is configured to be slidable from the slit 24C and insertable into the internal space 24D of the holding portion 24.

With this configuration, it is not necessary to slide the belt-like member 21 in a direction opposite to one direction (direction in which the diameter of the ring is reduced) while the belt-like member 21 is held by the holding portion 24. Therefore, it is not necessary to provide a configuration for releasing the locked state between the first locking portion 22 and the second locking portion 23 on the holding portion 24, and the holding portion 24 can be made compact. As a result, the holding portion 24 can easily enter the bag-shaped portion 16. In addition, since the structure is simple, there is also an advantage that the manufacturing cost can be reduced.

In addition, in the present embodiment, the second locking portion 23 is formed at a position (position separated from width clamping surface $24B_{-1}$ serving as a base point of rotation of the upper and lower clamping surfaces $24A_{-2}$ and $24A_{-2}$) eccentrically located toward the slit 24C side from the center position in the width direction of the belt-like member 21. As a result, it is possible to facilitate the work of sliding and inserting a portion of the belt-like member 21 into the internal space 24D from the outside of the holding portion 24 through the slit 24C.

In the above embodiment, the headphone cover 1A having a shape in which the fabric 11 is formed in a tubular shape and the tubular both-end openings $12_{-1}$ and $12_{-2}$ are formed has been described, but the shape of the headphone cover 1A is not limited thereto. For example, it may be the headphone covers 1B and 1C having a shape as illustrated in FIG. 13 or FIG. 14.

Figure 13:
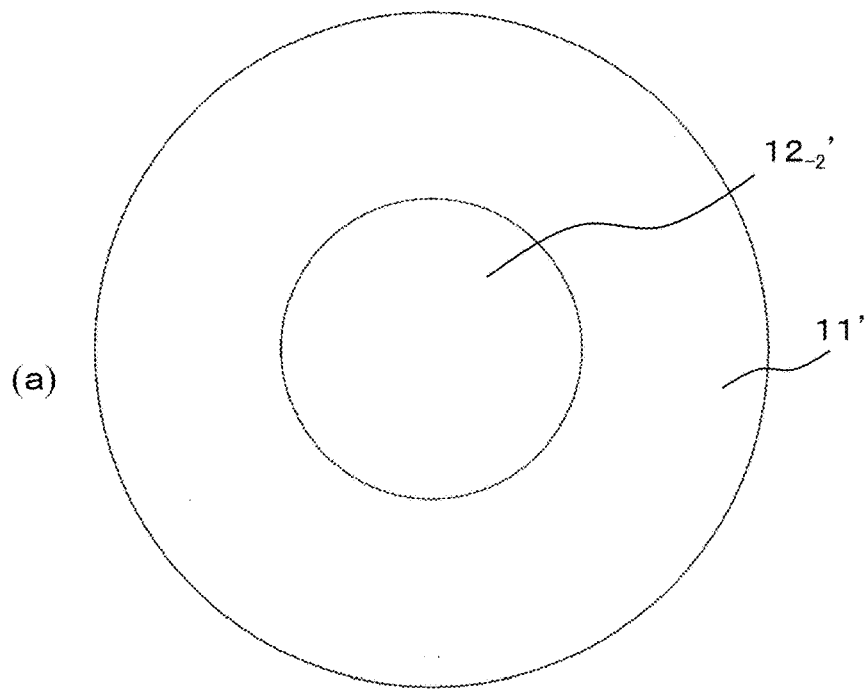
FIG. 13 is a diagram illustrating another configuration example of the headphone cover according to the present embodiment.
Figure 13:
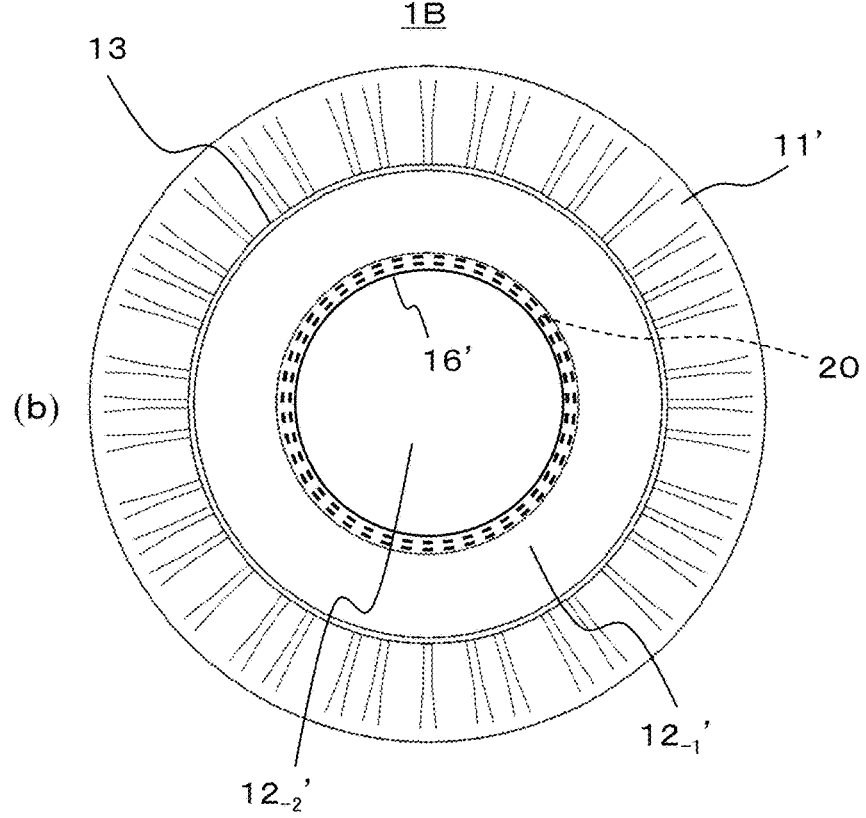
Figure 14:
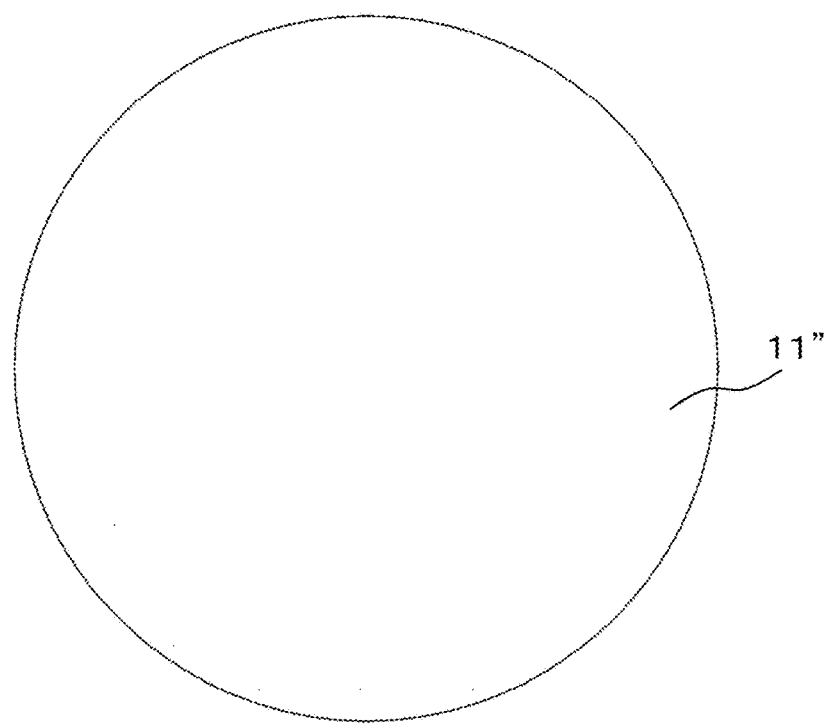
FIG. 14 is a diagram illustrating another configuration example of the headphone cover according to the present embodiment.
Figure 14:
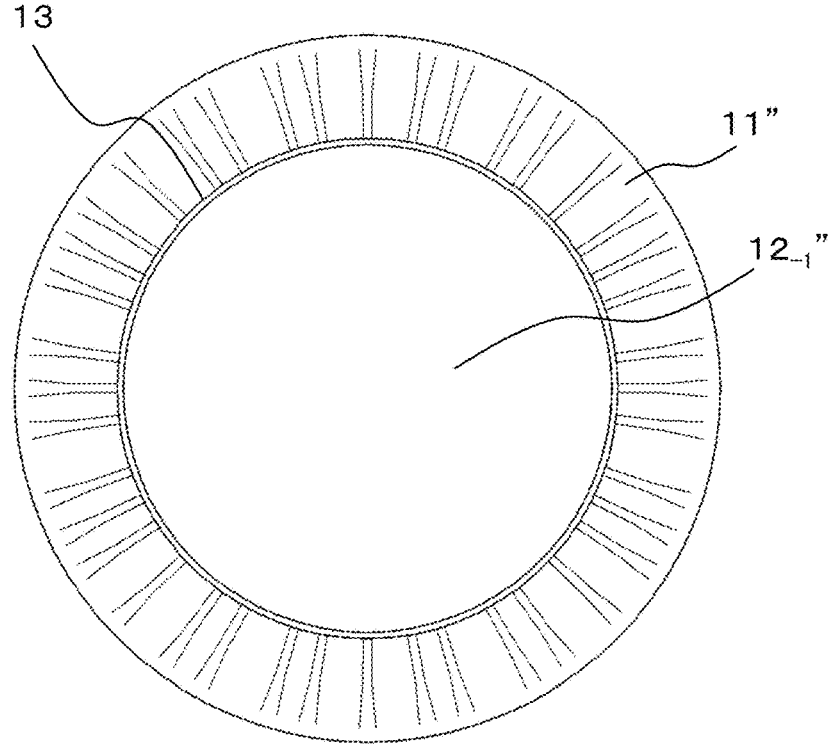

In FIG. 13, with (a) illustrating a upper surface (plan view) and (b) illustrating a lower surface (bottom surface). The headphone cover 1B in FIG. 13 has elasticity and is deformable. FIG. 13 illustrates one aspect of the shape of the headphone cover 1B in a steady state in which no external force is applied.

A peripheral edge portion of a fabric 11' is folded back to bottom surface side over the entire circumference. A first opening $12_{-1}$' is formed on the bottom surface side, and a second opening $12_{-2}$' is formed on a non-folded surface side (flat surface side) opposite to the bottom surface side. Both of the two openings $12_{-1}$' and $12_{-2}$' are formed in a circular shape, and the second opening $12_{-2}$' is formed to have a smaller diameter than the first opening $12_{-1}$'.

The first opening peripheral edge portion corresponding to the peripheral edge of the first opening $12_{-1}$' is provided with an elastic body (for example, elastic webbing) 13 for fixing the first opening peripheral edge portion to the outer peripheral surface of the ear pad 101 or the outer peripheral surface of the housing 102. Furthermore, a bag-shaped portion 16' is formed at a second opening peripheral edge portion corresponding to a peripheral edge of the second opening $12_{-2}$', and the fixing member 20 is inserted and embedded therein.

Even in the state that the ear pad 101 is covered with the fabric 11 of the headphone cover 1B with a configuration like FIG. 13 (similar to the state in FIG. 2), the cylindrical recessed space 105 formed in the middle portion of the ear pad 101 can be prevented from being blocked by the fabric 11 of the headphone cover 1B. This enables the user to use an around ear type headphone 100 attached with the headphone cover 1B with a sense of use similar to that of an around ear type.

In FIG. 14, with (a) illustrating a upper surface (plan view) and (b) illustrating a lower surface (bottom surface). The headphone cover 1C in FIG. 14 also has elasticity and is deformable. FIG. 14 illustrates one aspect of the shape of the headphone cover 1C in a steady state in which no external force is applied.

The peripheral edge portion of a fabric 11" is folded back to bottom surface side over the entire circumference, and an opening $12_{-1}$" is formed on the bottom surface side. The opening $12_{-1}$" is the same as the first opening $12_{-1}$' in the headphone cover 1B illustrated in FIG. 13. In the headphone cover 1C illustrated in FIG. 14, the second opening $12_{-2}$' in the headphone cover 1B does not exist.

The opening peripheral edge portion corresponding to the peripheral edge of the opening $12_{-1}$" is provided with an elastic body (for example, elastic webbing) 13 for fixing the opening peripheral edge portion to the outer peripheral surface of the ear pad 101 or the outer peripheral surface of the housing 102. The headphone cover 1C illustrated in FIG. 14 does not include the bag-shaped portion 16 for embedding the fixing member 20.

In the case of the headphone cover 1C illustrated in FIG. 14, the fixing member 20 fixes a part of the non-folded fabric 11" on the flat surface side opposite to the bottom surface side of the fabric 11" to the inner peripheral surface or the like of the ear pad 101. The part of the fabric 11" means a portion around the position where the opening peripheral edge portion of the second opening $12_{-2}$' of the headphone cover 1B illustrated in FIG. 13 exists.

Figure 15:
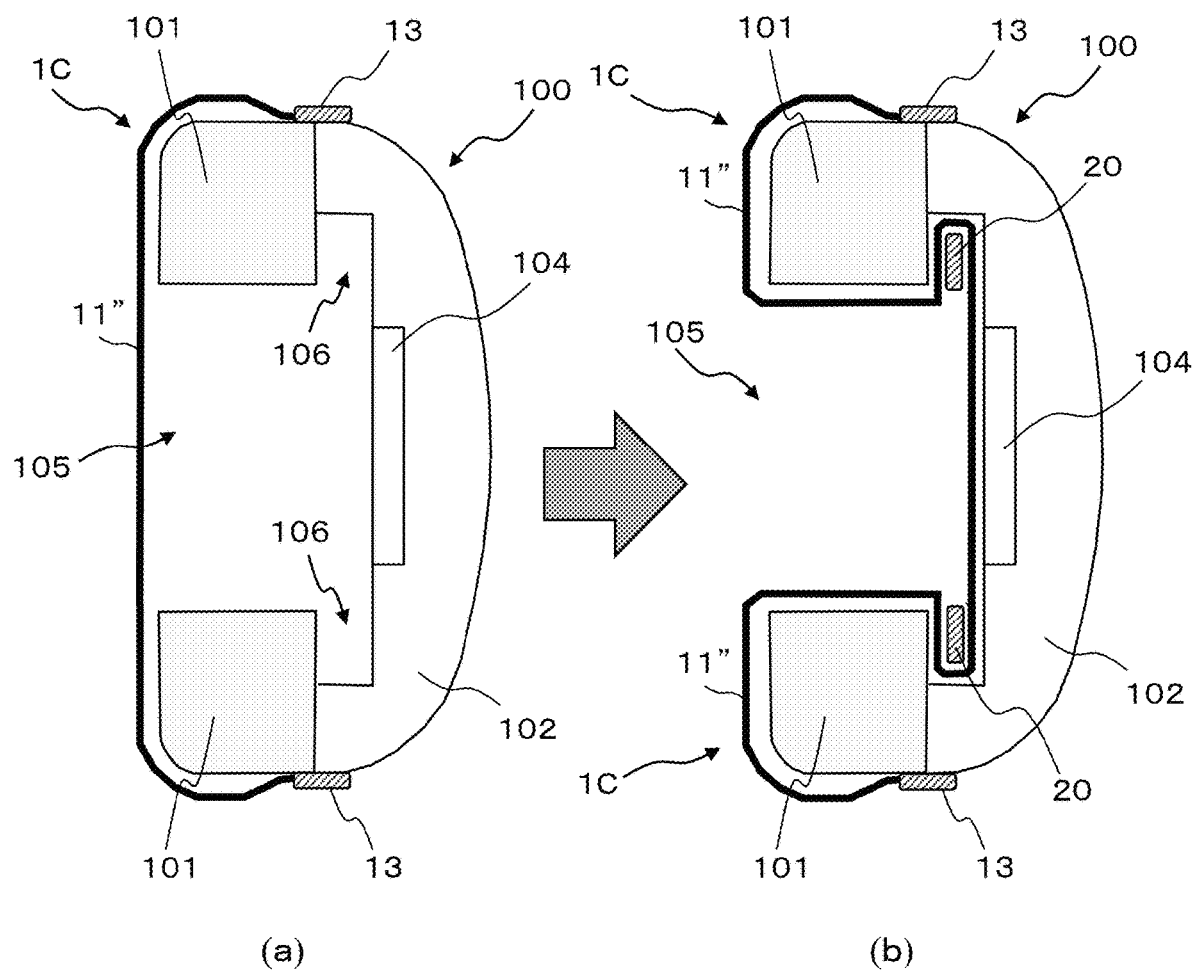
FIG. 15 is a schematic diagram illustrating a state in which the headphone covers illustrated in FIG. 14 are attached to the headphone.

FIG. 15 is a schematic diagram illustrating a state in which the headphone covers 1C are attached to the headphone 100. When the headphone cover 1C is to be attached to the headphone 100, first of all, as illustrated in FIG. 15(a), the opening $12_{-1}$" of the fabric 11" is expanded so that the entire ear pad 101 is covered with the fabric 11", and the elastic webbing 13 sewn to the opening peripheral edge portion of the fabric 11" is hooked on the outer peripheral surface of the ear pad 101 or the housing 102, so that the opening peripheral edge portion is fixed to the outer peripheral surface of the ear pad 101 or the housing 102. At this stage, the fabric 11" closes the cylindrical recessed space 105.

Next, as illustrated in FIG. 15(b), while extending the fabric 11" that closes the cylindrical recessed space 105 and pushing down the fabric 11" toward the bottom of the ear pad 101, by pressing the fixing member 20 formed into a ring shape against the fabric 11" from above so as to expand the diameter of the ring, the fixing member 20 is pressed into the gap 106 between the ear pad 101 and the housing 102 together with the part of the fabric 11". Thus, the ear pad 101 is covered with the fabric 11" in a state in which a part of the fabric 11" is fixed in the gap 106.

In this way, even when the ear pad 101 is covered with the fabric 11" of the headphone cover 1C, the cylindrical recessed space 105 formed in the middle portion of the ear pad 101 can be prevented from being blocked by the fabric 11" of the headphone cover 1C. This enables the user to use an around ear type headphone 100 attached with the headphone cover 1C according to the present embodiment with a sense of use similar to that of an around ear type.

In the above embodiment, an example has been described in which the slit 24C is provided in the holding portion 24 and a portion of the belt-like member 21 can be inserted into the internal space 24D of the holding portion 24 from the slit 24C, but the slit 24C may not be provided. For example, it is conceivable that one upper and lower clamping surface $24A_{-1}$ is configured separately from the other three clamping surfaces, and the one upper and lower clamping surface $24A_{-1}$ is configured rotatable with an end portion thereof as a base point. However, in this case, a mechanism for opening the internal space 24D by making one upper and lower clamping surface $24A_{-1}$ rotatable, a mechanism for closing the internal space 24D by locking the one upper and lower clamping surface $24A_{-1}$, and the like are required, and the structure becomes complicated. In this respect, it is more preferable to use a structure in which the slit 24C is provided as in the above embodiment.

Furthermore, in the above embodiment, an example in which the second locking portion 23 is provided at a position eccentrically located toward the slit 24C side from the center position in the width direction of the belt-like member 21 has been described, but the present invention is not limited thereto. For example, the second locking portion 23 may be provided at the center position in the width direction of the belt-like member 21. However, in this case, the amount of bending of the holding portion 24 required to insert the belt-like member 21 from the slit 24C increases. In this respect, it is preferable to provide the second locking portion 23 at a position eccentrically located on the slit 24C side as in the above-described embodiment.

Figure 16:
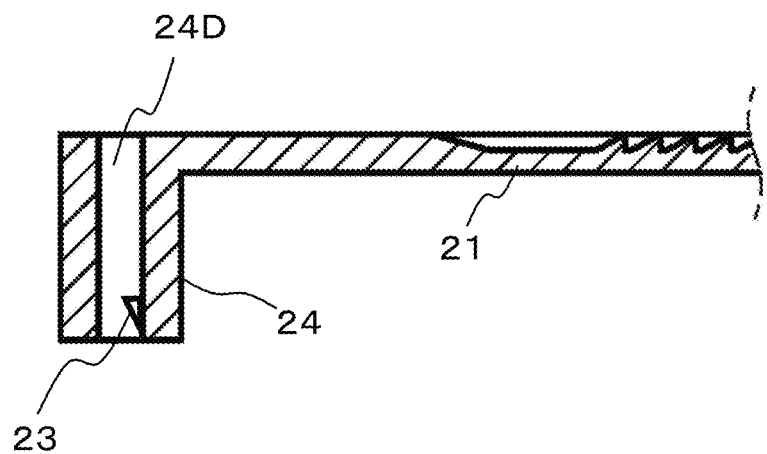
FIG. 16 is a diagram illustrating another configuration example of the fixing member according to the present embodiment.

Furthermore, in the above embodiment, an example in which the holding portion 24 is provided in parallel to the belt-like member 21 and the internal space 24D is formed in parallel to the belt-like member 21 has been described, but the present invention is not limited thereto. For example, as illustrated in FIG. 16, the holding portion 24 may be provided perpendicular to the belt-like member 21, and the internal space 24D may be perpendicular to the belt-like member 21. In this case, the second locking portion 23 is formed inside the holding portion 24. Note that even when the holding portion 24 is provided in parallel to the belt-like member 21 as in the above-described embodiment, the second locking portion 23 may be formed inside the holding portion 24.

Figure 17:
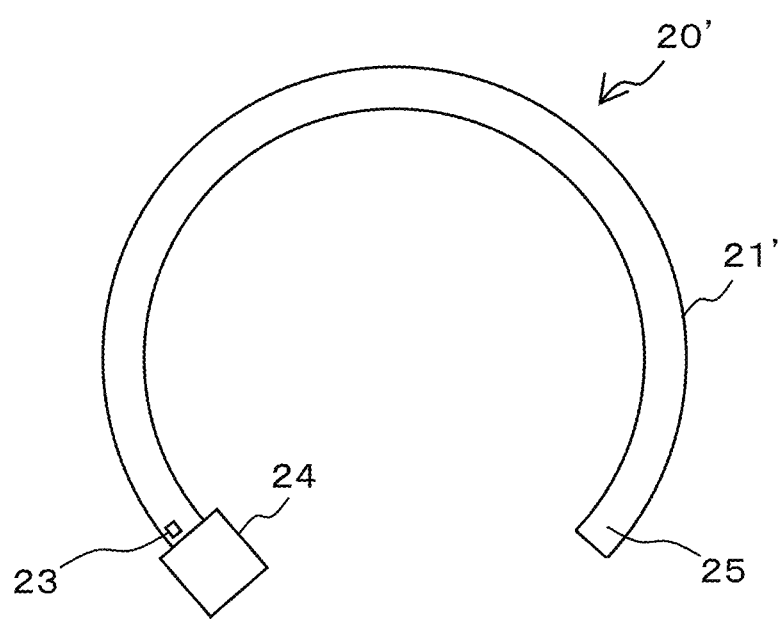
FIG. 17 is a diagram illustrating another configuration example of the fixing member according to the present embodiment.

Furthermore, in the above-described embodiment, an example of using a shape in which a constant width and a constant thickness linearly continue to be elongated, and opposing elongated planes (planes parallel to the pair of upper and lower clamping surfaces $24A_{-1}$ and $24A_{-2}$) formed thereby are linear, that is, the shape of the plane is rectangular has been described as the belt-like member 21. However, a shape in which a constant width and a constant thickness non-linearly continue to be elongated may be used. As an example, as illustrated in FIG. 17 in a state in which a fixing member 20' is viewed from the lower surface, a belt-like member 21' may have a shape in which a constant width and a constant thickness are elongated in an arc shape.

In this case, after the belt-like member 21' is bent in a direction (direction in which the terminal end portion 25 of the belt-like member 21' approaches the holding portion 24) in which the radius of the arc decreases, the belt-like member 21' is inserted into the internal space 24D of the holding portion 24 from the slit 24C, so that the ring state is formed such that the left and right side surfaces of the belt-like member 21' face the inside and the outside of the ring. Thereafter, when the fabric 11 is fixed to the inner wall of the ear pad 101, the belt-like member 21' is slid in the holding portion 24 in a direction in which the radius of the arc formed into a ring shape increases.

In the above embodiment, the configuration in which the first locking portion 22 and the second locking portion 23 are provided on the upper surface and the lower surface (surfaces parallel to the pair of upper and lower clamping surfaces $24A_{-1}$ and $24A_{-2}$) of the belt-like member 21 has been described, but the present invention is not limited thereto. For example, the first locking portion 22 and the second locking portion 23 may be provided on the left and right side surfaces (surfaces parallel to the pair of width clamping surfaces $24B_{-1}$ and $24B_{-2}$) of the belt-like member 21. In this case, a slit narrower than the width of the belt-like member 21 is provided in one of the pair of upper and lower clamping surfaces $24A_{-1}$ and $24A_{-2}$, and the pair of width clamping surfaces $24B_{-1}$ and $24B_{-2}$ is made rotatable in a direction of expanding the width of the slit with the other of the pair of upper and lower clamping surfaces $24A_{-1}$ and $24A_{-2}$ as a base point.

Figure 18:
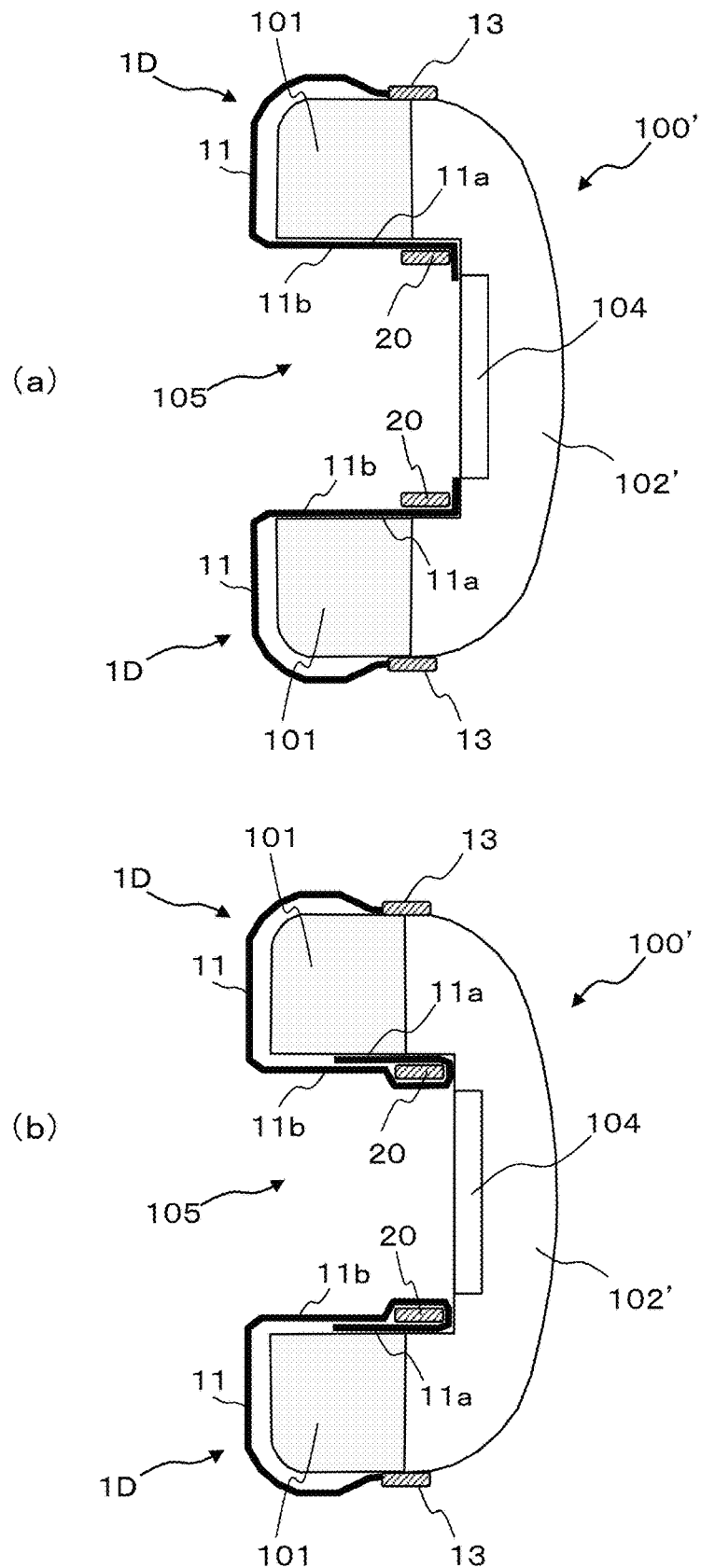
FIG. 18 is a diagram for explaining an example of a headphone cover attaching method

In addition, in the above embodiment, the configuration in which the fixing member 20 is embedded in the bag-shaped portion 16 formed in the second opening peripheral edge portion of the second opening $12_{-2}$ of the fabric 11 of the headphone cover 1A has been described, but the present invention is not limited thereto. For example, a headphone cover 1D may be configured without providing the bag-shaped portion 16 at the second opening peripheral edge portion as illustrated in FIG. 18, and the fabric 11 may be fixed to the inner peripheral surface or the like of the ear pad 101 by applying the fixing member 20 on the fabric 11 from the outside thereof as illustrated in FIG. 18(a).

Here, when the headphone cover 1D in which the cylindrical shape of the fabric 11 is configured large so as to be attachable on the headphone 100'(or 100) having a large size is attached to the relatively small headphone 100', if the fabric 11 is to be fitted to the inner peripheral surface of the ear pad 101 without any doubling, a remainder occurs on the front end side (the second opening $12_{-2}$ side where an elastic webbing 13 is not provided) of a part of the fabric 11 against which the fixing member 20 is pressed. Hereinafter, a portion of the fabric 11 fitted to the inner peripheral surface of the ear pad 101 is referred to as a fit portion 11b, and a remaining portion of the fabric 11 is referred to as a fabric remainder 11a.

When the fabric remainder 11a exists in the recessed space 105 of the ear pad 101, the fabric remainder 11a touches the ear of the user wearing the headphone 100', and may give discomfort to the user. Therefore, as illustrated in FIG. 18(b), the fabric 11 may be folded back at a position where the fixing member 20 is to be pressed to cover the fixing member 20, and the fabric 11 may be fixed to the inner peripheral surface or the like of the ear pad 101 by the fixing member 20 in a state in which a portion to be the fabric remainder 11a from the portion where the fabric 11 is folded back to the second opening $12_{-2}$ is clamped between the inner peripheral surface of the ear pad 101 and the fit portion 11b (portion where the fabric 11 is not folded back) of the fabric 11 or between the inner peripheral surface and the fixing member 20. Note that the fixing member 20 used to fix the headphone cover 1D as illustrated in FIG. 18(b) is not limited to the configuration illustrated in the above embodiment. For example, it may have a configuration disclosed in the specification and drawings of PCT/JP2019/014984.

Furthermore, in the above embodiment, the example in which the holding portion 24 is provided at the front end of the belt-like member 21 has been described, but the holding portion 24 may be provided at another position of the belt-like member 21. However, it is preferable in that the holding portion 24 is provided at the front end of the belt-like member 21, so that a length of a portion where the plurality of first locking portions 22 can be disposed can be maximized.

Furthermore, in the above embodiment, the example in which the belt-like member 21 of the fixing member 20 is made of resin has been described, but a shape memory alloy wire (memory wire) made of a metal material such as copper, brass, aluminum, stainless steel, or iron may be used.

In addition, the embodiments are merely examples of embodying the present invention, and the technical scope of the present invention should not be interpreted in a limited manner by these embodiments. That is, the present invention can be implemented in various forms without departing from the gist or main features of the present invention.

REFERENCE SIGNS LIST 1A, 1B, 1C, 1D headphone cover
11, 11', 11" fabric
$12_{-1}$, $12_{-2}$, $12_{-1}'$, $12_{-2}'$, $12_{-1}''$ opening
13 elastic webbing (elastic body)
16 bag-shaped portion
20 fixing member (fastener)
21 belt-like member
22 first locking portion
23 second locking portion
24 holding portion
24C slit
24D internal space
25 terminal end portion

The invention claimed is:

1. A headphone cover used covering an ear pad of an around ear type headphone, characterized by comprising:
a fabric including at least one opening and configured to cover the ear pad from an outer peripheral surface of the ear pad to an inner peripheral surface of the ear pad;
an elastic body that is provided in an opening peripheral edge portion corresponding to a peripheral edge of the opening and configured to fix the opening peripheral edge portion to an outer peripheral surface of the ear pad or an outer peripheral surface of a housing; and a fixing member that is disposed in a recessed space formed inside the ear pad and configured to fix a part of the fabric to an inner peripheral surface of the ear pad or a vicinity of inner peripheral surface,
the fixing member being a belt-like member having flexibility, and including
a plurality of first locking portions formed on one surface of the belt-like member,
a second locking portion formed on the other surface opposite to the one surface of the belt-like member, the second locking portion being in a locked state with any one of the plurality of first locking portions; and
a holding portion configured to slidably hold the belt-like member, wherein
the first locking portion and the second locking portion are configured in a shape in which the belt-like member is slidable only in one direction in which a length from an end portion of the belt-like member in a longitudinal direction to the portion held by the holding portion is shortened in a state in which the one portion of the belt-like member is held by the holding portion.

2. The headphone cover according to claim 1, characterized in that the holding portion is provided at one end of the belt-like member in a longitudinal direction, and configured to slidably hold a portion other than the one end of the belt-like member.

3. The headphone cover according to claim 1, characterized in that
the holding portion includes
a pair of upper and lower clamping surfaces configured to clamp the belt-like member from directions of the one surface and the other surface, and
a pair of width clamping surfaces configured to clamp the belt-like member from a width direction, and
a slit is formed in any one of the pair of upper and lower clamping surfaces and the pair of width clamping surfaces, and the pair of upper and lower clamping surfaces or the pair of width clamping surfaces are configured to be rotatable in a direction of expanding the slit.

4. The headphone cover according to claim 3, characterized in that
a slit thinner than a thickness of the belt-like member is formed in one width clamping surface of the pair of width clamping surfaces, and the pair of upper and lower clamping surfaces is configured to be rotatable in a direction of expanding the thickness of the slit with the other width clamping surface of the pair of width clamping surfaces as a base point.

5. The headphone cover according to claim 4, characterized in that the pair of upper and lower clamping surfaces and the pair of width clamping surfaces are configured to form an internal space through which the belt-like member is insertable in a direction parallel to a longitudinal direction of the belt-like member, and a portion of the belt-like member can be inserted into the internal space from the slit.

6. The headphone cover according to claim 3, characterized in that the pair of upper and lower clamping surfaces and the pair of width clamping surfaces are configured to form an internal space through which the belt-like member is insertable in a direction parallel to a longitudinal direction of the belt-like member, and a portion of the belt-like member can be inserted into the internal space from the slit.

7. The headphone cover according to claim 3, characterized in that the second locking portion is formed at a position eccentrically located on the slit side with respect to a center position in the width direction of the belt-like member on the other surface of the belt-like member.

8. The headphone cover according to claim 1, characterized in that
the holding portion includes:
a pair of upper and lower clamping surfaces configured to clamp the belt-like member from directions of the one surface and the other surface;
a pair of width clamping surfaces configured to clamp the belt-like member from a width direction, and
an internal space through which the belt-like member is insertable in a direction parallel to the longitudinal direction of the belt-like member is formed by the pair of upper and lower clamping surfaces and the pair of width clamping surfaces.

9. The headphone cover according to claim 1, characterized in that a terminal end portion including an end portion in the longitudinal direction of the belt-like member is configured to be thicker than a thickness other than the terminal end portion.

10. The headphone cover according to claim 1, characterized in that
the fabric is formed into a tubular shape, a first opening is formed at one end of the tubular shape, and a second opening is formed at the other end of the tubular shape,
the elastic body is provided in a first opening peripheral edge portion corresponding to a peripheral edge of the first opening, and a bag-shaped portion for embedding the fixing member is provided in a second opening peripheral edge portion corresponding to a peripheral edge of the second opening.

11. The headphone cover according to claim 2, characterized in that
the holding portion includes
a pair of upper and lower clamping surfaces configured to clamp the belt-like member from directions of the one surface and the other surface, and
a pair of width clamping surfaces configured to clamp the belt-like member from a width direction, and
a slit is formed in any one of the pair of upper and lower clamping surfaces and the pair of width clamping surfaces, and the pair of upper and lower clamping surfaces or the pair of width clamping surfaces are configured to be rotatable in a direction of expanding the slit.

12. A fastener formed of a belt-like member and configured to fasten a headphone cover on an ear pad of an around ear type headphone, characterized by comprising:
a plurality of first locking portions formed on one surface of the belt-like member;
a second locking portion formed on the other surface opposite to the one surface of the belt-like member, the second locking portion being in a locked state with any one of the plurality of first locking portions; and
a holding portion configured to slidably hold the belt-like member, wherein
the first locking portion and the second locking portion are configured in a shape in which the belt-like member is slidable only in one direction in which a length from an end portion of the belt-like member in a longitudinal direction to the portion held by the holding portion is shortened in a state in which the one portion of the belt-like member is held by the holding portion.

13. The fastener of a headphone cover according to claim 12, characterized in that the holding portion is provided at one end of the belt-like member in a longitudinal direction, and configured to slidably hold a portion other than the one end of the belt-like member.

14. The fastener of a headphone cover according to claim 12, characterized in that
the holding portion includes
a pair of upper and lower clamping surfaces configured to clamp the belt-like member from directions of the one surface and the other surface,
a pair of width clamping surfaces configured to clamp the belt-like member from a width direction,
a slit is formed in any one of the pair of upper and lower clamping surfaces and the pair of width clamping surfaces, and the pair of upper and lower clamping surfaces or the pair of width clamping surfaces are configured to be rotatable in a direction of expanding the slit.

15. The fastener of a headphone cover according to claim 14, characterized in that
a slit thinner than a thickness of the belt-like member is formed in one width clamping surface of the pair of width clamping surfaces, and the pair of upper and lower clamping surfaces is configured to be rotatable in a direction of expanding the thickness of the slit with the other width clamping surface of the pair of width clamping surfaces as a base point.

16. The fastener of a headphone cover according to claim 14, characterized in that the pair of upper and lower clamping surfaces and the pair of width clamping surfaces are configured to form an internal space through which the belt-like member is insertable in a direction parallel to a longitudinal direction of the belt-like member, and a portion of the belt-like member can be inserted into the internal space from the slit.

17. The fastener of a headphone cover according to claim 14, characterizer in that the second locking portion is formed at a position eccentrically located on the slit side with respect to a center position in the width direction of the belt-like member on the other surface of the belt-like member.

18. The fastener of a headphone cover according to claim 12, characterized in that
the holding portion includes
a pair of upper and lower clamping surfaces configured to clamp the belt-like member from directions of the one surface and the other surface,
a pair of width clamping surfaces configured to clamp the belt-like member from a width direction, and
an internal space through which the belt-like member is insertable in a direction parallel to the longitudinal direction of the belt-like member is formed by the pair of upper and lower clamping surfaces and the pair of width clamping surfaces.

19. The fastener of a headphone cover according to claim 12, characterized in that a terminal end portion including an end portion in the longitudinal direction of the belt-like member is configured to be thicker than a thickness other than the terminal end portion.

20. A headphone cover attaching method for covering an ear pad of an around ear type headphone with a headphone cover and fixing a part of a fabric of the headphone cover to an inner peripheral surface of the ear pad or a vicinity of the inner peripheral surface with a fixing member, characterized by including:
a step of fixing an opening peripheral edge portion corresponding to a peripheral edge of one opening of the fabric formed in a tubular shape to the outer peripheral surface of the ear pad or the outer peripheral surface of a housing by an elastic body provided at the opening peripheral edge portion;
a step of folding back the fabric at a location of a part of the fabric against which the fixing member is pressed, and covering the fixing member with the fabric being folded back; and
a step of fixing a part of the fabric to an inner peripheral surface of the ear pad or a vicinity of the inner peripheral surface by the fixing member in a state in which a portion that is a remainder of the fabric from a portion where the fabric is folded back to the other opening on a side opposite to the one opening is clamped between the inner peripheral surface of the ear pad and the portion where the fabric is not folded back or between the inner peripheral surface of the ear pad and the fixing member.

* * * * *